United States Patent
Kamal et al.

(10) Patent No.: US 7,312,210 B2
(45) Date of Patent: Dec. 25, 2007

(54) PYRROLO[2,1-C][1,4]BENZODIAZEPINE COMPOUNDS AND PROCESSES FOR THE PREPARATION THEREOF

(75) Inventors: Ahmed Kamal, Hyderabad (IN); Ankati Hari Babu, Hyderabad (IN); Adhi Venkata Ramana, Hyderabad (IN); Earla Vijaya Bharathi, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/367,223

(22) Filed: Mar. 3, 2006

(65) Prior Publication Data
US 2007/0082891 A1    Apr. 12, 2007

(30) Foreign Application Priority Data
Nov. 10, 2005    (IN)    .......................... 3013/Del/2005

(51) Int. Cl.
*C07D 405/14*    (2006.01)
*A61K 31/551*    (2006.01)
(52) U.S. Cl. ...................... 514/220; 540/496
(58) Field of Classification Search ................ 540/496; 514/220
See application file for complete search history.

(56) References Cited

OTHER PUBLICATIONS

Gregson et al. (2001) Design, synethesis, and evaluation of a novel pyrrolobenzodiazepine DNA-interactive agent with highly efficient cross-linking ability and potent cytotoxicity. J. Med. Chem. 44:737-748.

Hurley et al. (1977) Pyrrolo(1,4)benzodiazepine antitumor antibiotics in vitro interaction of anthramycin, sibiromycin and tomaymycin with DNA using specifically radiolabelled molecules. Biochimica et Biophysica Acta. 475:521-535.

Kaplan et al. (1981) Anthramycin binding to deoxyribonucleic acid-mitomycin C complexes. Evidence for drug-induced deoxyribonucleic acid conformational change and cooperativity in mitromycin C binding. American Chemical Society. 20:7572-7582.

Kohn et al. (1970) Reaction of anthramycin with deoxyribonucleic acid. J. Mol. Biol. 51:551-571.

Thurston et al. (1996) Synthesis of sequence-selective C8-linked pyrrolo[2,1-c][1,4]benzodiazepine DNA interstrand cross-linking agents. J. Org. Chem. 61:8141-8147.

*Primary Examiner*—Bruck Kifle
(74) *Attorney, Agent, or Firm*—Knobbe Martens Olson & Bear LLP

(57) ABSTRACT

The present invention provides novel pyrrolo [2,1-c][1,4] benzodiazepine compounds. This invention also provides a process for the preparation of novel pyrrolo[2,1-c][1,4] benzodiazepine compounds. These novel pyrrolo [2,1-c][1, 4]benzodiazepine compounds are useful as antitumor agents. It also provides a process for the preparation of 7-methoxy-8-{n-[4-(2-oxo-2H-4-chromenyl)piperazino] alkyl}-oxy-(11aS)-1,2,3,11a-5H-pyrrolo[2,1-c][1,4]benzodiazepin-5-one and 7-methoxy-8-{n-[4-(7-alkoxy-8-methyl-2-oxo-2H-4-chromenyl)piperazino]alkyl}-oxy-(11aS)-1,2, 3,11a-5H-pyrrolo[2,1-c][1,4]. benzodiazepine-5-one with aliphatic chain length variations for these compounds.

12 Claims, 1 Drawing Sheet

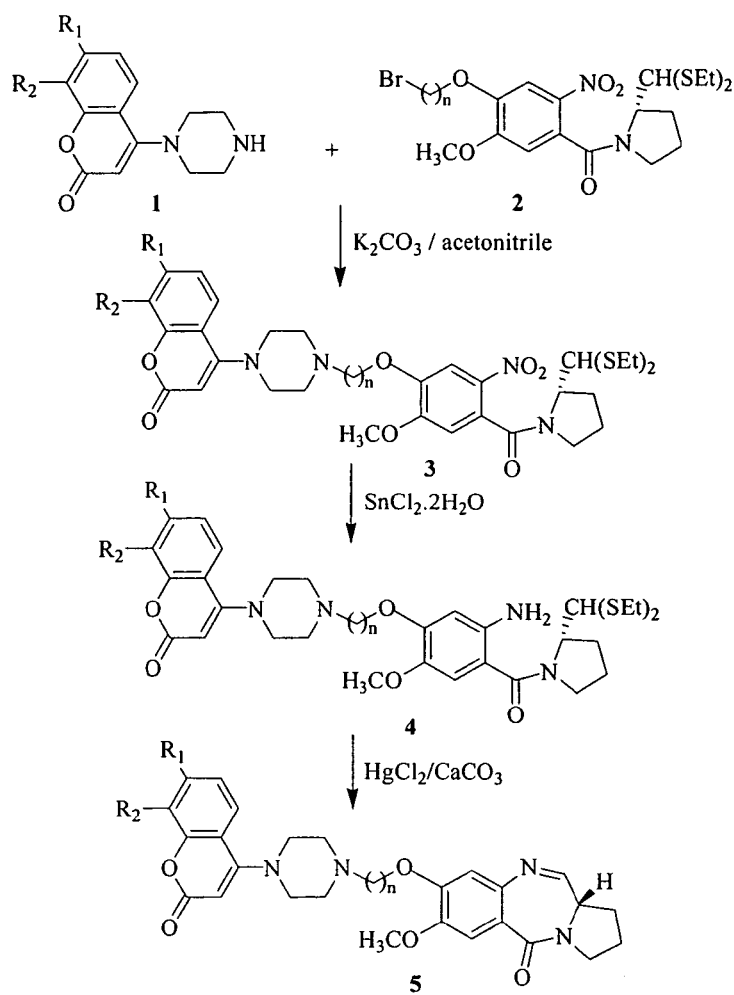
| compound | R₁ | R₂ | n |
|---|---|---|---|
| 5a | H | H | 3 |
| 5b | H | H | 4 |
| 5c | H | H | 5 |
| 5d | CH₃ | OCH₃ | 3 |
| 5e | CH₃ | OCH₃ | 4 |
| 5f | CH₃ | OCH₃ | 5 |
| 5g | CH₃ | OC₂H₅ | 3 |
| 5h | CH₃ | OC₂H₅ | 4 |
| 5i | CH₃ | OC₂H₅ | 5 |
| 5j | CH₃ | O $^i$C₃H₇ | 3 |
| 5k | CH₃ | O $^i$C₃H₇ | 4 |
| 5l | CH₃ | O $^i$C₃H₇ | 5 |
Scheme-1

PYRROLO[2,1-C][1,4]BENZODIAZEPINE COMPOUNDS AND PROCESSES FOR THE PREPARATION THEREOF

CROSS-REFERENCE TO RELATED APPLICATIONS

This application claims the benefit of Indian Patent Application No. 3013/DEL/2005 filed Nov. 10, 2005, the disclosure of which is incorporated herein in its entirety by reference.

BACKGROUND OF THE INVENTION

1. Field of the Invention

The present invention relates to novel pyrrolo[2,1-c][1,4] benzodiazepine compounds. This invention also relates to a process for the preparation of novel pyrrolo[2,1-c][1,4] benzodiazepine compounds. These novel pyrrolo[2,1-c][1,4]benzodiazepine compounds are useful as antitumor agents. More particularly, they relate to a process for the preparation of 7-methoxy-8-{n-[4-(2-oxo-2H-4-chromenyl) piperazino]alkyl}-oxy-(11aS)-1,2,3,11a-5H-pyrrolo[2,1-c] [1,4]benzodiazepin-5-one and 7-methoxy-8-{n-[4-(7-alkoxy-8-methyl-2-oxo-2H-4-chromenyl)piperazino] alkyl}-oxy-(11aS)-1,2,3,11a-5H-pyrrolo[2,1-c][1,4] benzodiazepine-5-one with aliphatic chain length variations for these compounds. The structural formula of these novel pyrrolo[2,1-c][1,4]benzodiazepines is given below.

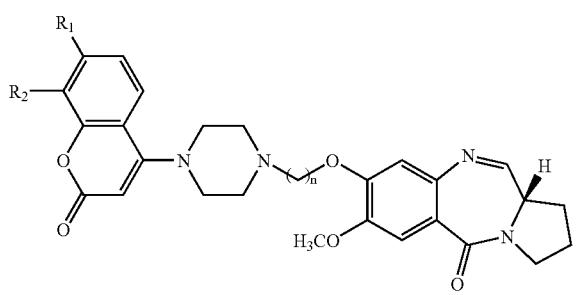

wherein $R_1$ is H or an alkoxy group selected from methoxy, ethoxy and propoxy groups, $R_2$ is H or $CH_3$ and n is an integer varying from 3-5.

2. Description of the Related Art

Pyrrolo[2,1-c][1,4]benzodiazepine antitumor antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665.; Kohn, K. W. and Speous, C. L. *J. Mol. Biol.*, 1970, 51, 551.; Hurley, L. H.; Gairpla, C. and Zmijewski, M. *Biochem. Biophys. Acta.*, 1977, 475, 521.; Kaplan, D. J. and Hurley, L. H. *Biochemistry*, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.* 1996, 61, 8141).

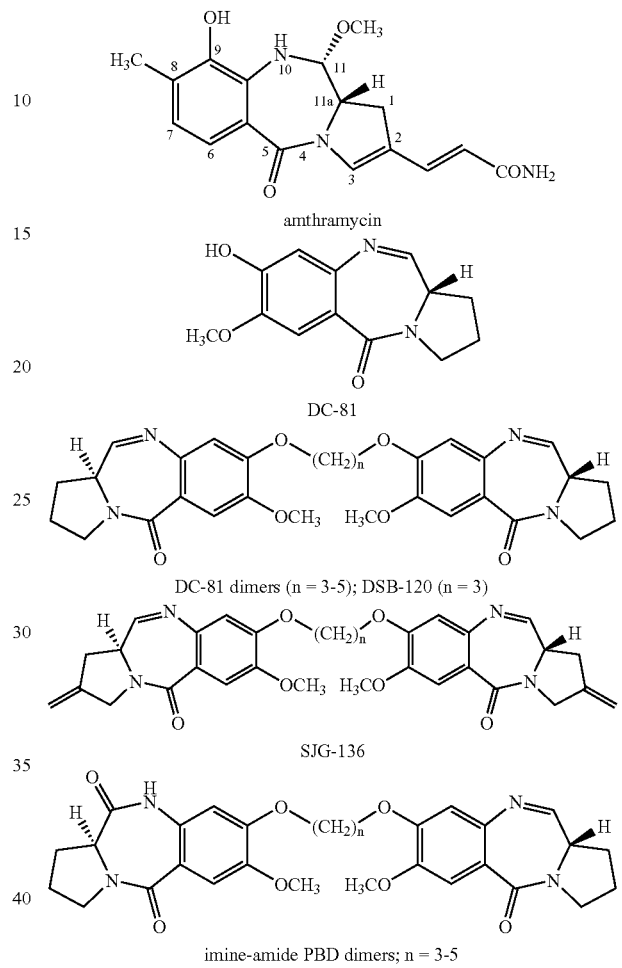

Recently, PBD dimers have been developed that comprise two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). Recently, a noncross-linking mixed imine-amide PBD dimers have been synthesized that have significant DNA binding ability and potent antitumor activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679).

Naturally occurring pyrrolo[2,1-c][1,4]benzodiazepines belong to a group of antitumor antibiotics derived from *Streptomyces* species. Recently, there is much impetus for the PBD systems as they can recognize and bind to specific sequence of DNA. Examples of naturally occurring PBD's include anthramycin, DC-81, tomaymycin, sibiromycin and neothramycin.

However, the clinical efficacy for these antibiotics is hindered by several limitations, such as poor water solubility, cardiotoxicity, development of drug resistance and metabolic inactivation.

SUMMARY OF THE INVENTION

Accordingly the present invention provides novel pyrrolo[2,1-c][1,4]benzodiazepines of formula 5

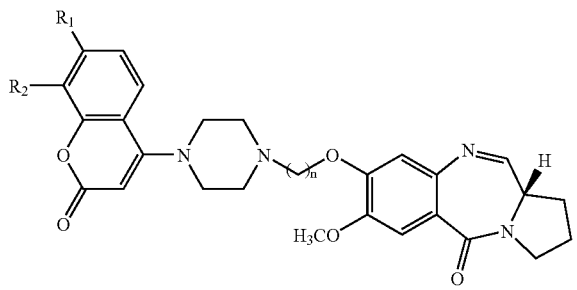

5 wherein $R_1$ is H or alkoxy group selected from methoxy, ethoxy and propoxy groups, $R_2$ is H or $CH_3$ and n is an integer varying from 3-5.

In an embodiment of the present invention the compound obtained is selected from the group consisting of 7-Methoxy-8-{3-[4-(2-oxo-2H-4-chromenyl)piperazino]propyl}-oxy-(11aS)-1,2,3,11a-5H-pyrrolo[2,1-c][1,4]benzodiazepin-5-one(5a), 7-Methoxy-8-{4-[4-(2-oxo-2H-4-chromenyl)piperazino]butyl}-oxy-(11aS)-1,2,3,11a-5H-pyrrolo[2,1-c][1,4]benzodiazepin-5-one(5b), 7-Methoxy-8-{5-[4-(2-oxo-2H-4-chromenyl)piperazino]pentyl}-oxy-(11aS)-1,2,3,11a-5H-pyrrolo[2,1-c][1,4]benzodiazepin-5-one(5c), 7-Methoxy-8-{3-[4-(7-methoxy-8-methyl-2-oxo-2H-4-chromenyl)piperazino]propyl}-oxy-(11aS)-1,2,3,11a-5H-pyrrolo[2,1-c][1,4]benzodiazepin-5-one(5d), 7-Methoxy-8-{4-[4-(7-methoxy-8-methyl-2-oxo-2H-4-chromenyl)piperazino]butyl}-oxy-(11aS)-1,2,3,11a-5H-pyrrolo[2,1-c][1,4]benzodiazepin-5-one(5e), 7-Methoxy-8-{5-[4-(7-methoxy-8-methyl-2-oxo-2H-4-chromenyl)piperazino]pentyl}-oxy-(11aS)-1,2,3,11a-5H-pyrrolo[2,1-c][1,4]benzodiazepin-5-one(5f), 7-Methoxy-8-{3-[4-(7-ethoxy-8-methyl-2-oxo-2H-4-chromenyl)piperazino]propyl}-oxy-(11aS)-1,2,3,11a-5H-pyrrolo[2,1-c][1,4]benzodiazepin-5-one(5g), 7-Methoxy-8-{4-[4-(7-ethoxy-8-methyl-2-oxo-2H-4-chromenyl)piperazino]butyl}-oxy}-(11aS)-1,2,3,11a-5H-pyrrolo[2,1-c][1,4]benzodiazepin-5-one(5h), 7-Methoxy-8-{5-[4-(7-ethoxy-8-methyl-2-oxo-2H-4-chromenyl)piperazino]pentyl}-oxy-(11a S)-1,2,3,11a-5H-pyrrolo[2,1-c][1,4]benzodiazepin-5-one(5i), 7-Methoxy-8-{3-[4-(7-isopropoxy-8-methyl-2-oxo-2H-4-chromenyl)piperazino]propyl}-oxy-(11aS)-1,2,3,11a-5H-pyrrolo[2,1-c][1,4]benzodiazepin-5-one(5j), 7-Methoxy-8-{4-[4-(7-isopropoxy-8-methyl-2-oxo-2H-4-chromenyl)piperazino]butyl}-oxy-(11aS)-1,2,3,11a-5H-pyrrolo[2,1-c][1,4]benzodiazepin-5-one(5k), 7-Methoxy-8-{5-[4-(7-isopropoxy-8-methyl-2-oxo-2H-4-chromenyl)piperazino]pentyl}-oxy-(11aS)-1,2,3,11a-5H-pyrrolo[2,1-c][1,4]benzodiazepin-5-one(5l).

In yet another embodiment the pyrrolo[2,1-c][1,4]benzodiazepines are active against human tumor cell lines derived from cancer types selected from the group consisting of leukemia, non-small-cell-lung cancer, colon cancer, CNS cancer, melanoma, ovarian cancer, renal cancer, prostate cancer and breast cancer.

In yet another embodiment the novel compound pyrrolo[2,1-c][1,4]benzodiazepine exhibits in vitro antitumoric activity when a dose of −5 to −8 $Log_{10}$ (mol/L), −4 to −7 $Log_{10}$ (mol/L) and −3 to −5 $Log_{10}$ (mol/L) of the said compound is exposed for at least 48 hrs to about sixty human tumor cells derived from nine cancer types such as leukemia, non-small-cell-lung cancer, colon cancer, CNS cancer, melanoma, ovarian cancer, renal cancer, prostate cancer, breast cancer, for GI50, TGI and LC50, respectively.

The present invention further provides a pharmaceutical composition comprising novel pyrrolo[2,1-c][1,4]benzodiazepines and derivatives, analogues, salts or mixture thereof optionally with pharmaceutically acceptable carriers.

In yet another embodiment the novel pyrrolo[2,1-c][1,4]benzodiazepine compounds used comprises the compound of general formula 5

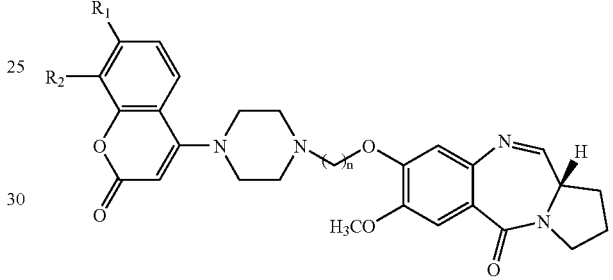

5 wherein $R_1$ is H or alkoxy group selected from methoxy, ethoxy and propoxy groups, $R_2$ is H or $CH_3$ and n is an integer varying from 3-5.

The present invention further provides a process for the preparation of novel pyrrolo[2,1-c][1,4]benzodiazepine of formula 5

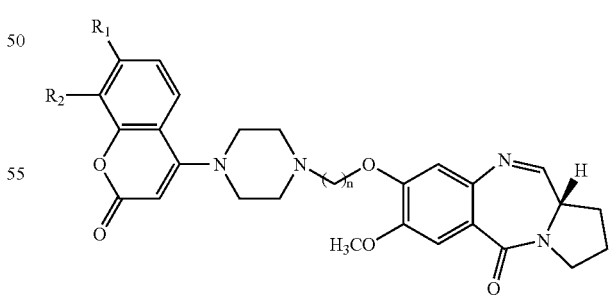

5 wherein $R_1$ is H or alkoxy group selected from methoxy, ethoxy and propoxy groups, $R_2$ is H or $CH_3$ and n is an integer varying from 3-5, the said process comprising the steps of:

reacting 4-piperazino-2H-2-chromenone or 7-alkoxy-8-methyl-4-piperazino-2H-2-chromenone of formula 1

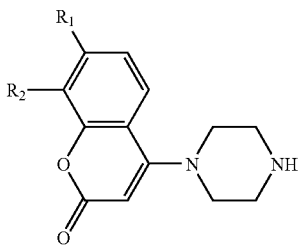

1 wherein $R_1$ is H or alkoxy group selected from methoxy, ethoxy and propoxy groups, $R_2$ is H or $CH_3$ and n is an integer varying from 3-5 with (2S)-N-[4-(n-bromoalkyl)-oxy-5-methoxy-2-nitrobenzoyl]pyrrolidine-2-carboxaldehyde diethylthioacetal of formula 2

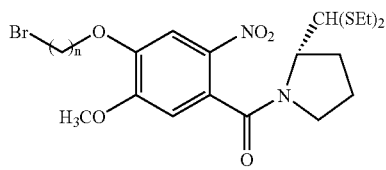

2 in presence of a base, in a dry organic solvent, for a period of about 48 h under reflux, followed by extraction in water and isolating the compound of (2S)-N-{4-[4-[n-[4-(2-oxo-2H-2-chromenyl)piperazino]alkyl]oxy]-5-methoxy-2-nitrobenzoyl}pyrrolidine-2-carboxaldehyde diethylthioacetal or (2S)-N-{4-[4-[n-[4-(7-alkyloxy-8-methyl-2-oxo-2H-2-chromenyl)piperazino]alkyl]oxy]-5-methoxy-2-nitrobenzoyl}pyrrolidine-2-carboxaldehyde diethylthioacetal of formula 3 by known methods,

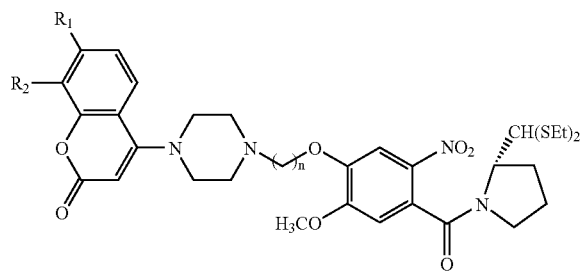

3 wherein $R_1$ is H or alkoxy group selected from methoxy, ethoxy and propoxy groups, $R_2$ is H or $CH_3$ and n is an integer varying from 3-5, reducing the above said nitro compound of formula 3 with $SnCl_2.2H_2O$ or an acid catalyst in presence of an organic solvent, under reflux, for a period of 1-2 hrs, followed by neutralizing the resultant reaction mixture at a pH of about 8 and isolating the amino compound (2S)-N-{4-[4-[n-[4-(2-oxo-2H-2-chromenyl)piperazino]alkyl]oxy]-5-methoxy-2-aminobenzoyl}pyrrolidine-2-carboxaldehyde diethylthioacetal or (2S)-N-{4-[4-[n-[4-(7-methoxy-8-methyl-2-oxo-2H-2-chromenyl)piperazino]alkyl]oxy]-5-methoxy-2-amino benzoyl}pyrrolidine-2-carboxaldehyde diethylthioacetal of formula 4 by known methods,

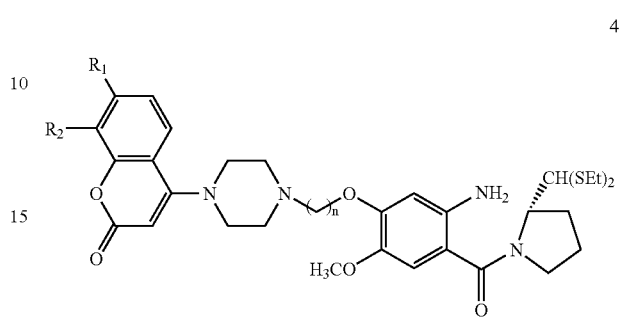

4 wherein $R_1$ is H or alkoxy group selected from methoxy, ethoxy and propoxy groups, $R_2$ is H or $CH_3$ and n is an integer varying from 3-5, reacting the above said amino compound of formula 4 with de-protecting agent in the presence of a aqueous organic solvent, at a temperature in the range of 20-25° C., for a period of about 12 hrs, separating the organic layer from the resultant reaction mixture followed by evaporation under vacuum to obtain the residue and diluting the above said residue with ethyl acetate followed by slowly mixing with saturated sodium bicarbonate, filtering, washing and evaporating the resultant filtrate, followed by purification by known methods to obtain the desired pyrrolo[2,1-c][1,4] benzodiazepine compound of formula 5.

In yet another embodiment the compound the base used in step (a) is selected from $K_2CO_3$ and $Na_2CO_3$.

In yet another embodiment the compound the organic solvent used in step (a) is selected from acetonitrile, acetone and N,N-demethyl formamide.

In yet another embodiment the compound the acid catalyst used in step (b) is selected from the group consisting of Sn/HCl, Zn/$CH_3COOH$ and Pd/C—$H_2$.

In yet another embodiment the organic solvent used in step (b) is selected from methanol, ethanol and ethylacetate.

In yet another embodiment the compound the de-protecting agent used in step (c) is selected from the group consisting of $HgCl_2/CaCO_3$, $HgO/HgCl_2$ and $Bi(OTf)_3.xH_2O$.

In yet another embodiment the organic solvent used in step (c) is selected from acetonitrile, dichloromethane and chloroform.

In yet another embodiment the compound obtained from the above said process is represented by a group of the following compounds:

7-Methoxy-8-{3-[4-(2-oxo-2H-4-chromenyl)piperazino]propyl}-oxy-(11aS)-1,2,3,11a-5H-pyrrolo[2,1-c][1,4]benzodiazepin-5-one(5a), 7-Methoxy-8-{4-[4-(2-oxo-2H-4-chromenyl)piperazino]butyl}-oxy-(11aS)-1,2,3,11a-5H-pyrrolo[2,1-c][1,4]benzodiazepin-5-one(5b), 7-Methoxy-8-{5-[4-(2-oxo-2H-4-chromenyl)piperazino]pentyl}-oxy-(11aS)-1,2,3,11a-5H-pyrrolo[2,1-c][1,4]benzodiazepin-5-one(5c), 7-Methoxy-8-{3-[4-(7-methoxy-8-methyl-2-oxo-2H-4-chromenyl)piperazino]propyl}-oxy-(11aS)-1,2,3,11a-5H-pyrrolo[2,1-c][1,4]benzodiazepin-5-one(5d), 7-Methoxy-8-{4-[4-(7-methoxy-8-methyl-2-oxo-2H-4-chromenyl)piperazino]butyl}-oxy-(11aS)-1,2, 3,11a-5H-pyrrolo[2,1-c][1,4]benzodiazepin-5-one(5e), 7-Methoxy-8-{5-[4-(7-methoxy-8-methyl-2-oxo-2H-4-chromenyl)piperazino]pentyl}-oxy-(11aS)-1,2,3,11a-5H-pyrrolo[2,1-c][1,4]benzodiazepin-5-one(5f), 7-Methoxy-8-{3-[4-(7-ethoxy-8-methyl-2-oxo-2H-4-chromenyl)piperazino]propyl}-oxy-(11aS)-1,2,3,11a-5H-pyrrolo[2,1-c][1,4]benzodiazepin-5-one(5g), 7-Methoxy-8-{4-[4-(7-ethoxy-8-methyl-2-oxo-2H-4-chromenyl)piperazino]butyl}-oxy}-(11aS)-1,2,3,11a-5H-pyrrolo[2,1-c][1,4]benzodiazepin-5-one(5h), 7-Meth oxy-8-{5-[4-(7-ethoxy-8-methyl-2-oxo-2H-4-chromenyl)piperazino]pentyl}-oxy-(11aS)-1,2,3,11a-5H-pyrrolo[2,1-c][1,4]benzodiazepin-5-one(5i), 7-Methoxy-8-{3-[4-(7-isopropoxy-8-methyl-2-oxo-2H-4-chromenyl)piperazino]propyl}-oxy-(11aS)-1,2,3,11a-5H-pyrrolo[2,1-c][1,4]benzodiazepine-5-one(5j), 7-Methoxy-8-{4-[4-(7-isopropoxy-8-methyl-2-oxo-2H-4-chromenyl)piperazino]butyl}-oxy-(11aS)-1,2,3,11a-5H-pyrrolo[2,1-c][1,4]benzodiazepin-5-one(5k), 7-Methoxy-8-{5-[4-(7-isopropoxy-8-methyl-2-oxo-2H-4-chromenyl)piperazino]pentyl}-oxy-(11aS)-1,2,3,11a-5H-pyrrolo[2,1-c][1,4]benzodiazepin-5-one(5l).

BRIEF DESCRIPTION OF THE DRAWINGS

FIG. 1 shows a synthetic pathway according to certain present embodiments and a table listing the various R groups and values for n in the compounds 5a, 5b, 5c, 5d, 5e, 5f, 5g, 5h, 5i, 5j, 5k and 5l.

DETAILED DESCRIPTION OF THE INVENTION

These new pyrrolo[2,1-c][1,4]benzodiazepine compounds linked at C-8 position have shown promising DNA binding activity and efficient anticancer activity in various cell lines. The molecules synthesized are of immense biological significance with potential sequence selective DNA-binding property. This resulted in design and synthesis of new congeners as illustrated in FIG. 1, which comprise:
1. The ether linkage at C-8 position of DC-81 intermediates with 4-piperazino-2H-2-chromenone/7-alkoxy-8-methyl-4-piperazino-2H-2-chromenone moiety.
2. Refluxing the reaction mixtures for 48 h.
3. Synthesis of C-8 linked PBD antitumor antibiotic hybrid imines.
4. Purification by column chromatography using different solvents like ethyl acetate, hexane, dichloromethane and methanol.

The following examples are given by way of illustration and therefore should not be construed to limit the scope of the invention.

EXAMPLE 1

To a solution of (2S)-N-[4-(3-bromopropyl)-oxy-5-methoxy-2-nitrobenzoyl]pyrrolidine-2-carboxaldehyde diethylthioacetal of formula 2 (521 mg, 1.0 mmol), 4-piperazino-2H-2-chromenone of formula 1 (230 mg, 1.0 mmol) and $K_2CO_3$ (414 mg, 3.0 mmol), in dry acetonitrile (40 ml) was refluxed for 48 hrs. After the completion of the reaction as indicated by TLC, EtOAc:hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[3-[4-(2-oxo-2H-2-chromenyl)piperazino]propyl]oxy]-5-methoxy-2-nitrobenzoyl}pyrrolidine-2-carboxaldehyde diethylthioacetal 3

$H^1$ NMR ($CDCl_3$, 200 MHz): δ 1.20-1.40 (m, 8H), 1.70-2.40 (m, 4H), 2.50-2.85 (m, 6H), 3.15-3.30 (m, 6H), 3.40-3.80 (m, 4H), 3.95 (s, 3H), 4.0-4.15 (t, 2H, J=6.04 Hz), 4.60-4.70 (m, 1H), 4.80-4.85 (m, 1H), 5.70 (s, 1H), 6.80 (s, 1H), 7.15-7.25 (t, 1H, J=7.55 Hz), 7.28-7.45 (d, 1H, J=7.55 Hz), 7.40-7.50 (t, 1H, J=7.55 Hz), 7.52-7.56 (d, 1H, J=7.55 Hz), 7.65 (s, 1H) MS (FAB) 671 $[M+H]^+$ (2S)-N-{4-[4-[3-[4-(2-Oxo-2H-2-chromenyl)piperazino]propyl]oxy]-5-methoxy-2-nitrobenzoyl}pyrrolidine-2-carboxaldehyde diethylthioacetal of formula 3 (670 mg, 1.0 mmol) was dissolved in methanol (10 mL) and to this was added $SnCl_2.2H_2O$ (1.125 g, 5 mmol) and was refluxed for 1.5 h. The reaction mixture was neutralized to pH 8 with $NaHCO_3$ solution and then extracted with ethyl acetate (3×20 ml). The combined organic phase was dried over $Na_2SO_4$ and evaporated under reduced pressure to afford the crude (2S)-N-{4-[4-[3-[4-(2-oxo-2H-2-chromenyl)piperazino]propyl]oxy]-5-methoxy-2-aminobenzoyl}pyrrolidine-2-carboxaldehyde diethylthioacetal 4

To a solution of (2S)-N-{4-[4-[3-[4-(2-oxo-2H-2-chromenyl)piperazino]propyl]oxy]-5-methoxy-2-aminobenzoyl}pyrrolidine-2-carboxaldehyde diethylthioacetal of formula 4 (640 mg, 1 mmol), $HgCl_2$ (613 mg, 2.26 mmol) and $CaCO_3$ (246 mg, 2.46 mmol) in $CH_3CN/H_2O$ (4:1) was stirred at room temperature for 12 h until the completion of the reaction as shown by TLC (EtOAc). The organic layer is evaporated in vacuum and the residue is diluted with EtOAc. To this, saturated $NaHCO_3$ was added slowly at room temperature and the mixture was filtered through a celite bed and washed with ethyl acetate. The filtrate was evaporated in vacuum to get crude 7-methoxy-8-{3-[4-(2-oxo-2H-4-chromenyl)piperazino]propyl}-oxy-(11aS)-1,2,3,11a-5H-pyrrolo[2,1-c][1,4]benzodiazepin-5-one 5, which was further purified by column chromatography on silica gel eluting first with ethyl acetate to remove traces of mercuric salts and then with $CHCl_3$:methanol (9:1).

$H^1$ NMR ($CDCl_3$, 200 MHz): δ 1.80-1.90 (m, 2H), 2.20-2.60 (m, 4H), 2.80-2.90 (m, 4H), 3.25-3.40 (m, 4H), 3.45-3.85 (m, 4H), 3.90 (s, 3H), 4.15-4.30 (m, 3H), 5.70 (s, 1H), 6.85 (s, 1H), 7.15-7.20 (t, 1H, J=6.69 Hz), 7.30-7.38 (d, 1H, J=8.18 Hz), 7.44-7.50 (d, 1H, J=8.18 Hz), 7.55-7.59 (t, 1H, J=7.43 Hz), 7.62 (s, 1H), 7.64-7.68 (d, 1H, J=3.72 Hz); MS (FAB) 517 $[M+H]^+$

EXAMPLE 2

To a solution of (2S)-N-[4-(4-bromobutyl)-oxy-5-methoxy-2-nitrobenzoyl]pyrrolidine-2-carboxaldehyde diethylthioacetal of formula 2 (535 mg, 1.0 mmol), 4-piperazino-2H-2-chromenone of formula 1 (230 mg, 1.0 mmol) and $K_2CO_3$ (414 mg, 3.0 mmol), in dry acetonitrile (40 ml) was refluxed for 48 hrs. After the completion of the reaction as indicated by TLC, EtOAc:hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[4-[4-(2-oxo-2H-2-chromenyl)piperazino]butyl]oxy]-5-methoxy-2-nitrobenzoyl}pyrrolidine-2-carboxaldehyde diethylthioacetal 3

H$^1$ NMR (CDCl$_3$, 200 MHz): δ 1.20-1.40 (m, 6H), 1.65-2.35 (m, 8H), 2.60-2.85 (m, 6H), 3.15-3.30 (m, 6H), 3.40-3.80 (m, 4H), 3.95 (s, 3H), 4.0-4.15 (t, 2H, J=6.04 Hz), 4.60-4.70 (m, 1H), 4.80-4.85 (m, 1H), 5.65 (s, 1H), 6.80 (s, 1H), 7.18-7.20 (t, 1H, J=7.55 Hz), 7.25-7.35 (d, 1H, J=8.68 Hz), 7.40-7.50 (t, 1H, J=6.93 Hz), 7.55-7.60 (d, 1H, J=7.93 Hz), 7.61 (s, 1H) MS (FAB) 685 [M+H]$^+$ (2S)-N-{4-[4-[4-[4-(2-Oxo-2H-2-chromenyl)piperazino]butyl]oxy]-5-methoxy-2-nitrobenzoyl}pyrrolidine-2-carboxaldehyde diethylthioacetal of formula 3 (684 mg, 1.0 mmol) was dissolved in methanol (10 mL) and to this was added SnCl$_2$.2H$_2$O (1.125 g, 5 mmol) and was refluxed for 1.5 h. The reaction mixture was neutralized to pH 8 with NaHCO$_3$ solution and then extracted with ethyl acetate (3×20 ml). The combined organic phase was dried over Na$_2$SO$_4$ and evaporated under reduced pressure to afford the crude (2S)-N-{4-[4-[4-[4-(2-oxo-2H-2-chromenyl)piperazino]butyl]oxy]-5-methoxy-2-amino benzoyl}pyrrolidine-2-carboxaldehyde diethylthioacetal 4

To a solution of (2S)-N-{4-[4-[4-[4-(2-oxo-2H-2-chromenyl)piperazino]butyl]oxy]-5-methoxy-2-aminobenzoyl}pyrrolidine-2-carboxaldehyde diethylthioacetal of formula 4 (654 mg, 1 mmol), HgCl$_2$ (613 mg, 2.26 mmol) and CaCO$_3$ (246 mg, 2.46 mmol) in CH$_3$CN/H$_2$O (4:1) was stirred at room temperature for 12 h until the completion of the reaction as shown by TLC (EtOAc). The organic layer is evaporated in vacuum and the residue is diluted with EtOAc. To this, saturated NaHCO$_3$ was added slowly at room temperature and the mixture was filtered through a celite bed and washed with ethyl acetate. The filtrate was evaporated in vacuum to get crude 7-methoxy-8-{4-[4-(2-oxo-2H-4-chromenyl)piperazino]butyl}-oxy-(11aS)-1,2,3,11a-5H-pyrrolo[2,1-c][1,4]benzodiazepin-5-one 5, which was further purified by column chromatography on silica gel eluting first with ethyl acetate to remove traces of mercuric salts and then with CHCl$_3$: methanol (9:1).

H$^1$ NMR (CDCl$_3$, 200 MHz): δ 1.80-2.00 (m, 4H), 2.20-2.60 (m, 4H), 2.70-2.90 (m, 4H), 3.25-3.40 (m, 4H), 3.60-3.85 (m, 4H), 3.90 (s, 3H), 4.15-4.30 (m, 3H), 5.70 (s, 1H), 6.82 (s, 1H), 7.15-7.20 (t, 1H, J=6.69 Hz), 7.30-7.38 (d, 1H, J=8.18 Hz), 7.44-7.50 (d, 1H, J=8.18 Hz), 7.55-7.59 (t, 1H, J=7.43 Hz), 7.62 (s, 1H), 7.64-7.68 (d, 1H, J=3.72 Hz); MS (FAB) 531 [M+H]$^+$

EXAMPLE 3

To a solution of (2S)-N-[4-(5-bromopentyl)-oxy-5-methoxy-2-nitrobenzoyl]pyrrolidine-2-carboxaldehyde diethylthioacetal of formula 2 (549 mg, 1.0 mmol), 4-piperazino-2H-2-chromenone of formula 1 (230 mg, 1.0 mmol) and K$_2$CO$_3$ (414 mg, 3.0 mmol), in dry acetonitrile (40 ml) was refluxed for 48 hrs. After the completion of the reaction as indicated by TLC, EtOAc:hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[5-[4-(2-oxo-2H-2-chromenyl)piperazino]pentyl]oxy]-5-methoxy-2-nitrobenzoyl}pyrrolidine-2-carboxaldehyde diethylthioacetal 3

H$^1$ NMR (CDCl$_3$, 200 MHz): δ 1.20-1.40 (m, 8H), 1.70-2.40 (m, 6H), 2.60-2.85 (m, 8H), 3.15-3.35 (m, 6H), 3.40-3.80 (m, 4H), 3.95 (s, 3H), 4.10-4.25 (t, 2H, J=6.04 Hz), 4.60-4.70 (m, 1H), 4.80-4.85 (m, 1H), 5.70 (s, 1H), 6.80 (s, 1H), 7.18-7.20 (t, 1H, J=7.55 Hz), 7.25-7.35 (d, 1H, J=8.68 Hz), 7.40-7.50 (t, 1H, J=6.93 Hz), 7.55-7.60 (d, 1H, J=7.93 Hz), 7.61 (s, 1H) MS (FAB) 699 [M+H]$^+$ (2S)-N-{4-[4-[5-[4-(2-Oxo-2H-2-chromenyl)piperazino]pentyl]oxy]-5-methoxy-2-nitrobenzoyl}pyrrolidine-2-carboxaldehyde diethylthioacetal of formula 3 (698 mg, 1.0 mmol) was dissolved in methanol (10 mL) and to this was added SnCl$_2$.2H$_2$O (1.125 g, 5 mmol) and was refluxed for 1.5 h. The reaction mixture was neutralized to pH 8 with NaHCO$_3$ solution and then extracted with ethyl acetate (3×20 ml). The combined organic phase was dried over Na$_2$SO$_4$ and evaporated under reduced pressure to afford the crude (2S)-N-{4-[4-[5-[4-(2-oxo-2H-2-chromenyl)piperazino]pentyl]oxy]-5-methoxy-2-aminobenzoyl}pyrrolidine-2-carboxaldehyde diethylthioacetal 4

To a solution of (2S)-N-{4-[4-[5-[4-(2-oxo-2H-2-chromenyl)piperazino]pentyl]oxy]-5-methoxy-2-aminobenzoyl}pyrrolidine-2-carboxaldehyde diethylthioacetal of formula 4 (668 mg, 1 mmol), HgCl$_2$ (613 mg, 2.26 mmol) and CaCO$_3$ (246 mg, 2.46 mmol) in CH$_3$CN/H$_2$O (4:1) was stirred at room temperature for 12 h until the completion of the reaction as shown by TLC (EtOAc). The organic layer is evaporated in vacuum and the residue is diluted with EtOAc. To this, saturated NaHCO$_3$ was added slowly at room temperature and the mixture was filtered through a celite bed and washed with ethyl acetate. The filtrate was evaporated in vacuum to get crude 7-methoxy-8-{5-[4-(2-oxo-2H-4-chromenyl)piperazino]pentyl}-oxy-(11aS)-1,2,3,11a-5H-pyrrolo[2,1-c][1,4]benzo diazepin-5-one 5, which was further purified by column chromatography on silica gel eluting first with ethyl acetate to remove traces of mercuric salts and then with CHCl$_3$: methanol (9:1).

H$^1$ NMR (CDCl$_3$, 200 MHz): δ 2.08-2.20 (m, 6H), 2.22-2.60 (m, 4H), 2.63-2.82 (m, 4H), 3.25-3.40 (m, 4H), 3.45-3.85 (m, 4H), 3.90 (s, 3H), 4.15-4.25 (m, 3H), 5.68 (s, 1H), 6.82 (s, 1H), 7.15-7.20 (t, 1H, J=6.69 Hz), 7.30-7.38 (d, 1H, J=8.18 Hz), 7.44-7.50 (d, 1H, J=8.18 Hz), 7.55-7.59 (t, 1H, J=7.43 Hz), 7.62 (s, 1H), 7.64-7.68 (d, 1H, J=3.72 Hz) MS (FAB) 545 [M+H]$^+$

EXAMPLE 4

To a solution of (2S)-N-[4-(3-bromopropyl)-oxy-5-methoxy-2-nitrobenzoyl]pyrrolidine-2-carboxaldehyde diethylthioacetal of formula 2 (521 mg, 1.0 mmol), 7-methoxy-8-methyl-4-piperazino-2H-2-chromenone of formula 1 (274 mg, 1.0 mmol) and K$_2$CO$_3$ (414 mg, 3.0 mmol), in dry acetonitrile (40 ml) was refluxed for 48 hrs. After the completion of the reaction as indicated by TLC, EtOAc: hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[3-[4-(7-methoxy-8-methyl-2-oxo-2H-2-chromenyl)piperazino]propyl]oxy]-5-methoxy-2-nitrobenzoyl}pyrrolidine-2-carboxaldehyde diethylthioacetal 3

H$^1$ NMR (CDCl$_3$, 200 MHz): δ 1.20-1.40 (m, 8H), 1.90-2.19 (m, 4H), 2.21 (s, 3H), 2.31-2.40 (t, 2H, J=7.85 Hz), 2.60-2.82 (m, 8H), 3.18-3.30 (m, 4H), 3.35-3.40 (t, 2H, J=7.07 Hz), 3.90 (s, 3H), 3.95 (s, 3H), 4.15-4.20 (m, 2H), 4.60-4.80 (m, 1H), 4.80-4.90 (m, 1H), 5.51 (s, 1H), 6.68-6.72 (d, 1H, J=8.64 Hz), 6.79 (s, 1H), 7.31-7.38 (d, 1H, J=9.43 Hz), 7.64 (s, 1H); MS (FAB) 715 [M+H]$^+$ (2S)-N-{4-[4-[3-[4-(7-Methoxy-8-methyl-2-oxo-2H-2-chromenyl)piperazino]propyl]oxy]-5-methoxy-2-nitrobenzoyl}pyrrolidine-2-carboxaldehyde diethylthioacetal of formula 3 (714 mg, 1.0 mmol) was dissolved in methanol (10 mL) and to this was added $SnCl_2.2H_2O$ (1.125 g, 5 mmol) and was refluxed for 1.5 h. The reaction mixture was neutralized to pH 8 with $NaHCO_3$ solution and then extracted with ethyl acetate (3×20 ml). The combined organic phase was dried over $Na_2SO_4$ and evaporated under reduced pressure to afford the crude (2S)-N-{4-[4-[3-[4-(7-methoxy-8-methyl-2-oxo-2H-2-chromenyl)piperazino]propyl]oxy]-5-methoxy-2-aminobenzoyl}pyrrolidine-2-carboxaldehyde diethylthioacetal 4

To a solution of (2S)-N-{4-[4-[3-[4-(7-methoxy-8-methyl-2-oxo-2H-2-chromenyl)piperazino]propyl]oxy]-5-methoxy-2-aminobenzoyl}pyrrolidine-2-carboxaldehyde diethylthioacetal of formula 4 (714 mg, 1 mmol), $HgCl_2$ (613 mg, 2.26 mmol) and $CaCO_3$ (246 mg, 2.46 mmol) in $CH_3CN/H_2O$ (4:1) was stirred at room temperature for 12 h until the completion of the reaction as shown by TLC (EtOAc). The organic layer is evaporated in vacuum and the residue is diluted with EtOAc. To this, saturated $NaHCO_3$ was added slowly at room temperature and the mixture was filtered through a celite bed and washed with ethyl acetate. The filtrate was evaporated in vacuum to get crude 7-methoxy-8-{3-[4-(7-methoxy-8-methyl-2-oxo-2H-4-chromenyl)piperazino]propyl}-oxy-(11aS)-1,2,3,11a-5H-pyrrolo[2,1-c][1,4]benzodiazepin-5-one 5, which was further purified by column chromatography on silica gel eluting first with ethyl acetate to remove traces of mercuric salts and then with $CHCl_3$:methanol (9:1).

$H^1$ NMR ($CDCl_3$, 200 MHz): δ 2.00-2.20 (m, 2H), 2.22-2.40 (m, 7H), 2.60-2.80 (m, 4H), 3.20-3.35 (m, 4H), 3.45-3.80 (m, 4H), 3.90 (s, 3H), 3.92 (s, 3H), 4.15-4.25 (m, 3H), 5.60 (s, 1H), 6.74-6.78 (d, 1H, J=8.91 Hz)), 6.84 (s, 1H), 7.38-7.42 (d, 1H, J=8.91 Hz), 7.50 (s, 1H), 7.64-7.68 (d, 1H, J=3.72 Hz); MS (FAB) 561 [M+H]+

EXAMPLE 5

To a solution of (2S)-N-[4-(4-bromobutyl)-oxy-5-methoxy-2-nitrobenzoyl]pyrrolidine-2-carboxaldehyde diethylthioacetal of formula 2 (535 mg, 1.0 mmol), 7-methoxy-8-methyl-4-piperazino-2H-2-chromenone of formula 1 (274 mg, 1.0 mmol) and $K_2CO_3$ (414 mg, 3.0 mmol), in dry acetonitrile (40 ml) was refluxed for 48 hrs. After the completion of the reaction as indicated by TLC, EtOAc:hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[4-[4-(7-methoxy-8-methyl-2-oxo-2H-2-chromenyl)piperazino]butyl]oxy]-5-methoxy-2-nitrobenzoyl}pyrrolidine-2-carboxaldehyde diethylthioacetal 3

$H^1$ NMR ($CDCl_3$, 200 MHz): δ 1.20-1.40 (m, 10H), 1.60-2.18 (m, 8H), 2.21 (s, 3H), 2.60-2.80 (m, 8H), 3.18-3.30 (m, 4H), 3.84 (s, 3H), 3.90 (s, 3H), 4.14-4.20 (m, 2H), 4.60-4.71 (m, 1H), 4.78-4.84 (m, 1H), 5.55 (s, 1H), 6.71-6.75 (d, 1H, J=8.92 Hz), 6.78 (s, 1H), 7.34-7.38 (d, 1H, J=8.18 Hz), 7.62 (s, 1H) MS (FAB) 729 [M+H]+

(2S)-N-{4-[4-[4-[4-(7-Methoxy-8-methyl-2-oxo-2H-2-chromenyl)piperazino]butyl]oxy]-5-methoxy-2-nitrobenzoyl}pyrrolidine-2-carboxaldehyde diethylthioacetal of formula 3 (728 mg, 1 mmol) was dissolved in methanol (10 mL) and to this was added $SnCl_2.2H_2O$ (1.125 g, 5 mmol) and was refluxed for 1.5 h. The reaction mixture was neutralized to pH 8 with $NaHCO_3$ solution and then extracted with ethyl acetate (3×20 ml). The combined organic phase was dried over $Na_2SO_4$ and evaporated under reduced pressure to afford the crude (2S)-N-{4-[4-[4-[4-(7-methoxy-8-methyl-2-oxo-2H-2-chromenyl)piperazino]butyl]oxy]-5-methoxy-2-aminobenzoyl}pyrrolidine-2-carboxaldehyde diethylthioacetal 4

To a solution of (2S)-N-{4-[4-[4-[4-(7-methoxy-8-methyl-2-oxo-2H-2-chromenyl)piperazino]butyl]oxy]-5-methoxy-2-aminobenzoyl}pyrrolidine-2-carboxaldehyde diethylthioacetal of formula 4 (698 mg, 1 mmol), $HgCl_2$ (613 mg, 2.26 mmol) and $CaCO_3$ (246 mg, 2.46 mmol) in $CH_3CN/H_2O$ (4:1) was stirred at room temperature for 12 h until the completion of the reaction as shown by TLC (EtOAc). The organic layer is evaporated in vacuum and the residue is diluted with EtOAc. To this, saturated $NaHCO_3$ was added slowly at room temperature and the mixture was filtered through a celite bed and washed with ethyl acetate. The filtrate was evaporated in vacuum to get crude 7-methoxy-8-{4-[4-(7-methoxy-8-methyl-2-oxo-2H-4-chromenyl)piperazino]butyl}-oxy-(11aS)-1,2,3,11a-5H-pyrrolo[2,1-c][1,4]benzodiazepin-5-one 5, which was further purified by column chromatography on silica gel eluting first with ethyl acetate to remove traces of mercuric salts and then with $CHCl_3$:methanol (9:1).

$H^1$ NMR ($CDCl_3$, 200 MHz): δ 1.90-2.10 (m, 4H), 2.20-2.40 (m, 7H), 2.60-2.80 (m, 4H), 3.20-3.35 (m, 4H), 3.45-3.80 (m, 4H), 3.90 (s, 3H), 3.92 (s, 3H), 4.15-4.25 (m, 3H), 5.60 (s, 1H), 6.74-6.78 (d, 1H, J=8.91 Hz), 6.84 (s, 1H), 7.38-7.42 (d, 1H, J=8.91 Hz), 7.50 (s, 1H), 7.64-7.68 (d, 1H, J=3.72 Hz); MS (FAB) 575 [M+H]+

EXAMPLE 6

To a solution of (2S)-N-[4-(5-bromopentyl)-oxy-5-methoxy-2-nitrobenzoyl]pyrrolidine-2-carboxaldehyde diethylthioacetal of formula 2 (549 mg, 1.0 mmol), 7-methoxy-8-methyl-4-piperazino-2H-2-chromenone of formula 1 (274 mg, 1.0 mmol) and $K_2CO_3$ (414 mg, 3.0 mmol), in dry acetonitrile (40 ml) was refluxed for 48 hrs. After the completion of the reaction as indicated by TLC, EtOAc:hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[5-[4-(7-methoxy-8-methyl-2-oxo-2H-2-chromenyl)piperzino]pentyl]oxy]-5-methoxy-2-nitrobenzoyl}pyrrolidine-2-carboxaldehyde diethylthioacetal 3

$H^1$ NMR ($CDCl_3$, 200 MHz): δ 1.20-1.40 (m, 8H), 1.40-1.70 (m, 4H), 1.82-2.18 (m, 4H), 2.21 (s, 3H), 2.47-2.55 (t, 2H, J=7.55 Hz), 2.62-2.82 (m, 8H), 3.20-3.30 (m, 4H), 3.32-3.42 (m, 2H), 3.90 (s, 3H), 3.95 (s, 3H), 4.05-4.13 (t, 2H, J=6.04 Hz), 4.62-4.70 (m, 1H), 4.80-4.84 (m, 1H), 5.50 (s, 1H), 6.68-6.78 (d, 1H, J=9.07 Hz), 6.80 (s, 1H), 7.32-7.40 (d, 1H, J=9.07 Hz), 7.65 (s, 1H) MS (FAB) 743 [M+H]+

(2S)-N-{4-[4-[5-[4-(7-Methoxy-8-methyl-2-oxo-2H-2-chromenyl)piperazino]pentyl]oxy]-5-methoxy-2-nitrobenzoyl}pyrrolidine-2-carboxaldehyde diethylthioacetal of formula 4 (742 mg, 1 mmol) was dissolved in methanol (10 mL) and to this was added $SnCl_2.2H_2O$ (1.125 g, 5 mmol) and was refluxed for 1.5 h. The reaction mixture was neutralized to pH 8 with $NaHCO_3$ solution and then extracted with ethyl acetate (3×20 ml). The combined organic phase was dried over Na$_2$SO$_4$ and evaporated under reduced pressure to afford the crude (2S)-N-{4-[4-[5-[4-(7-methoxy-8-methyl-2-oxo-2H-2-chromenyl)piperazino]pentyl]oxy]-5-methoxy-2-aminobenzoyl}pyrrolidine-2-carboxaldehyde diethylthioacetal 4

To a solution of (2S)-N-{4-[4-[5-[4-(7-methoxy-8-methyl-2-oxo-2H-2-chromenyl)piperazino]pentyl]oxy]-5-methoxy-2-aminobenzoyl}pyrrolidine-2-carboxaldehyde diethylthioacetal of formula 4 (712 mg, 1 mmol), HgCl$_2$ (613 mg, 2.26 mmol) and CaCO$_3$ (246 mg, 2.46 mmol), HgCl$_2$ (mmol) and CaCO$_3$ (mmol) in CH$_3$CN/H$_2$O (4:1) was stirred at room temperature for 12 h until the completion of the reaction as shown by TLC (EtOAc). The organic layer is evaporated in vacuum and the residue is diluted with EtOAc. To this, saturated NaHCO$_3$ was added slowly at room temperature and the mixture was filtered through a celite bed and washed with ethyl acetate. The filtrate was evaporated in vacuum to get crude 7-methoxy-8-{5-[4-(7-methoxy-8-methyl-2-oxo-2H-4-chromenyl)piperazino]pentyl}-oxy-(11aS)-1,2,3,11a-5H-pyrrolo[2,1-c][1,4]benzodiazepin-5-one 5, which was further purified by column chromatography on silica gel eluting first with ethyl acetate to remove traces of mercuric salts and then with CHCl$_3$: methanol (9:1).

H$^1$ NMR (CDCl$_3$, 200 MHz): δ 1.82-2.15 (m, 6H), 2.20-2.60 (m, 7H), 2.62-2.80 (m, 4H), 3.20-3.40 (m, 4H), 3.45-3.80 (m, 4H), 3.90 (s, 3H), 3.92 (s, 3H), 4.10-4.20 (m, 3H), 5.60 (s, 1H), 6.75-6.78 (d, 1H, J=9.43 Hz)), 6.80 (s, 1H), 7.38-7.42 (d, 1H, J=8.64 Hz), 7.50 (s, 1H), 7.64-7.68 (d, 1H, J=4.71 Hz); MS (FAB) 589 [M+H]$^+$

EXAMPLE 7

To a solution of (2S)-N-[4-(3-bromopropyl)-oxy-5-methoxy-2-nitrobenzoyl]pyrrolidine-2-carboxaldehyde diethylthioacetal of formula 2 (521 mg, 1.0 mmol), 7-ethoxy-8-methyl-4-piperazino-2H-2-chromenone of formula 1 (288 mg, 1.0 mmol) and K$_2$CO$_3$ (414 mg, 3.0 mmol), in dry acetonitrile (40 ml) was refluxed for 48 hrs. After the completion of the reaction as indicated by TLC, EtOAc: hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[3-[4-(7-ethoxy-8-methyl-2-oxo-2H-2-chromenyl)piperazino]propyl]oxy]-5-methoxy-2-nitrobenzoyl}pyrrolidine-2-carboxaldehyde diethylthioacetal 3

H$^1$ NMR (CDCl$_3$, 200 MHz): δ 1.20-1.40 (m, 8H), 1.44-1.50 (t, 3H, J=6.80 Hz), 1.50-2-00 (m, 4H), 2.30-2.40 (m, 5H), 2.60-3.00 (m, 8H), 3.18-3.40 (m, 6H), 3.90 (s, 3H), 4.02-4.20 (m, 4H), 4.60-4.70 (m, 1H), 4.80-4.82 (m, 1H), 5.60 (s, 1H), 6.68-6.75 (d, 1H, J=9.07 Hz), 6.80 (s, 1H), 7.28-7.38 (d, 1H, J=9.07 Hz), 7.62 (s, 1H); MS (FAB) 729 [M+H]$^+$ (2S)-N-{4-[4-[3-[4-(7-Ethoxy-8-methyl-2-oxo-2H-2-chromenyl)piperazino]propyl]oxy]-5-methoxy-2-nitrobenzoyl}pyrrolidine-2-carboxaldehyde diethylthioacetal of formula 3 (728 mg, 1 mmol) was dissolved in methanol (10 mL) and to this was added SnCl$_2$.2H$_2$O (1.125 g, 5 mmol) and was refluxed for 1.5 h. The reaction mixture was neutralized to pH 8 with NaHCO$_3$ solution and then extracted with ethyl acetate (3×20 ml). The combined organic phase was dried over Na$_2$SO$_4$ and evaporated under reduced pressure to afford the crude (2S)-N-{4-[4-[3-[4-(7-ethoxy-8-methyl-2-oxo-2H-2-chromenyl)piperazino]propyl]oxy]-5-methoxy-2-aminobenzoyl}pyrrolidine-2-carboxaldehyde diethylthioacetal 4

To a solution of (2S)-N-{4-[4-[3-[4-(7-ethoxy-8-methyl-2-oxo-2H-2-chromenyl)piperazino]propyl]oxy]-5-methoxy-2-aminobenzoyl}pyrrolidine-2-carboxaldehyde diethylthioacetal of formula 4 (698 mg, 1 mmol), HgCl$_2$ (613 mg, 2.26 mmol) and CaCO$_3$ (246 mg, 2.46 mmol), HgCl$_2$ (mmol) and CaCO$_3$ (mmol) in CH$_3$CN/H$_2$O (4:1) was stirred at room temperature for 12 h until the completion of the reaction as shown by TLC (EtOAc). The organic layer is evaporated in vacuum and the residue is diluted with EtOAc. To this, saturated NaHCO$_3$ was added slowly at room temperature and the mixture was filtered through a celite bed and washed with ethyl acetate. The filtrate was evaporated in vacuum to get crude 7-methoxy-8-{3-[4-(7-ethoxy-8-methyl-2-oxo-2H-4-chromenyl)piperazino]propyl}-oxy-(11aS)-1,2,3,11a-5H-pyrrolo[2,1-c][1,4]benzodiazepin-5-one 5, which was further purified by column chromatography on silica gel eluting first with ethyl acetate to remove traces of mercuric salts and then with CHCl$_3$ methanol (9:1).

H$^1$ NMR (CDCl$_3$, 200 MHz): δ 1.40-1.50 (t, 3H, J=6.65 Hz), 1.80-2.00 (m, 2H), 2.15 (s, 3H), 2.50-2.80 (m, 4H), 2.80-3.00 (m, 4H), 3.15-3.50 (m, 4H), 3.60-3.80 (m, 4H), 3.95 (s, 3H), 4.15-4.20 (m, 5H), 5.60 (s, 1H), 6.70-6.78 (d, 1H, J=8.34 Hz), 6.80 (s, 1H), 7.28-7.38 (d, 1H, J=8.34 Hz), 7.45 (s, 1H), 7.64-7.68 (d, 1H, J=3.74 Hz); MS (FAB) 575 [M+H]$^+$

EXAMPLE 8

To a solution of (2S)-N-[4-(4-bromobutyl)-oxy-5-methoxy-2-nitrobenzoyl]pyrrolidine-2-carboxaldehyde diethylthioacetal of formula 2 (535 mg, 1.0 mmol), 7-ethoxy-8-methyl-4-piperazino-2H-2-chromenone of formula 1 (288 mg, 1.0 mmol) and K$_2$CO$_3$ (414 mg, 3.0 mmol), in dry acetonitrile (40 ml) was refluxed for 48 hrs. After the completion of the reaction as indicated by TLC, EtOAc: hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[4-[4-(7-ethoxy-8-methyl-2-oxo-2H-2-chromenyl)piperazino]butyl]oxy]-5-methoxy-2-nitrobenzoyl}pyrrolidine-2-carboxaldehyde diethylthioacetal 3

H$^1$ NMR (CDCl$_3$, 200 MHz): δ 1.20-1.40 (m, 10H), 1.44-1.50 (t, 3H, J=6.80 Hz), 1.50-2-00 (m, 4H), 2.30-2.40 (m, 5H), 2.60-3.00 (m, 8H), 3.18-3.40 (m, 6H), 3.90 (s, 3H), 4.02-4.20 (m, 4H), 4.60-4.70 (m, 1H), 4.80-4.82 (m, 1H), 5.60 (s, 1H), 6.68-6.75 (d, 1H, J=9.07 Hz), 6.80 (s, 1H), 7.28-7.38 (d, 1H, J=9.07 Hz), 7.62 (s, 1H) MS (FAB) 743 [M+H]$^+$ (2S)-N-{4-[4-[4-[4-(7-Ethoxy-8-methyl-2-oxo-2H-2-chromenyl)piperazino]butyl]oxy]-5-methoxy-2-nitrobenzoyl}pyrrolidine-2-carboxaldehyde diethylthioacetal of formula 3 (742 mg, 1 mmol) was dissolved in methanol (10 mL) and to this was added SnCl$_2$.2H$_2$O (1.125 g, 5 mmol) and was refluxed for 1.5 h. The reaction mixture was neutralized to pH 8 with NaHCO$_3$ solution and then extracted with ethyl acetate (3×20 ml). The combined organic phase was dried over Na$_2$SO$_4$ and evaporated under reduced pressure to afford the crude (2S)-N-{4-[4-[4-[4-(7-ethoxy-8-methyl-2-oxo-2H-2-chromenyl)piperazino]butyl]oxy]-5-methoxy-2-aminobenzoyl}pyrrolidine-2-carboxaldehyde diethylthioacetal 4

To a solution of (2S)-N-{4-[4-[4-[4-(7-ethoxy-8-methyl-2-oxo-2H-2-chromenyl)piperazino]butyl]oxy]-5-methoxy-2-aminobenzoyl}pyrrolidine-2-carboxaldehyde diethylthioacetal of formula 4 (712 mg, 1 mmol), HgCl$_2$ (613 mg, 2.26 mmol) and CaCO$_3$ (246 mg, 2.46 mmol) in CH$_3$CN/H$_2$O (4:1) was stirred at room temperature for 12 h until the completion of the reaction as shown by TLC (EtOAc). The organic layer is evaporated in vacuum and the residue is diluted with EtOAc. To this, saturated NaHCO$_3$ was added slowly at room temperature and mixture was filtered through a celite bed and washed with ethyl acetate. The filtrate was evaporated in vacuum to get crude 7-methoxy-8-{4-[4-(7-ethoxy-8-methyl-2-oxo-2H-4-chromenyl)piperazino]butyl}-oxy}-(11aS)-1,2,3,11a-5H-pyrrolo[2,1-c][1,4]benzodiazepin-5-one 5, which was further purified by column chromatography on silica gel eluting first with ethyl acetate to remove traces of mercuric salts and then with CHCl$_3$:methanol (9:1).

H$^1$ NMR (CDCl$_3$, 200 MHz): δ 1.50-1.52 (t, 3H, J=7.04 Hz), 1.60-2.00 (m, 4H), 2.15 (s, 3H), 2.20-2.40 (m, 4H), 2.60-2.80 (m, 4H), 3.20-3.35 (m, 4H), 3.60-3.89 (m, 4H), 3.95 (s, 3H), 4.10-4.20 (m, 5H), 5.60 (s, 1H), 6.70-6.78 (d, 1H, J=8.64 Hz), 6.80 (s, 1H), 7.35-7.38 (d, 1H, J=8.64 Hz), 7.50 (s, 1H), 7.64-7.68 (d, 1H, J=3.93 Hz); MS (FAB) 589 [M+H]$^+$

EXAMPLE 9

To a solution of (2S)-N-[4-(5-bromopentyl)-oxy-5-methoxy-2-nitrobenzoyl]pyrrolidine-2-carboxaldehyde diethylthioacetal of formula 2 (549 mg, 1.0 mmol), 7-ethoxy-8-methyl-4-piperazino-2H-2-chromenone of formula 1 (288 mg, 1.0 mmol) and K$_2$CO$_3$ (414 mg, 3.0 mmol), in dry acetonitrile (40 ml) was refluxed for 48 hrs. After the completion of the reaction as indicated by TLC, EtOAc:hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[5-[4-(7-ethoxy-8-methyl-2-oxo-2H-2-chromenyl)piperazino]pentyl]oxy]-5-methoxy-2-nitrobenzoyl}pyrrolidine-2-carboxaldehyde diethylthioacetal 3

H$^1$ NMR (CDCl$_3$, 200 MHz): δ 1.20-1.40 (m, 12H), 1.40-1.50 (t, 3H, J=6.80 Hz), 1.62-2.18 (m, 8H), 2.21 (s, 3H), 2.45-2.82 (m, 8H), 3.18-3.30 (m, 4H), 3.90 (s, 3H), 4.02-4.20 (m, 4H), 4.60-4.70 (m, 1H), 4.78-4.82 (m, 1H), 0.5.59 (s, 1H), 6.68-6.72 (d, 1H, J=9.07 Hz), 6.80 (s, 1H), 7.28-7.38 (d, 1H, J=9.07 Hz), 7.62 (s, 1H) MS (FAB) 757 [M+H]$^+$ (2S)-N-{4-[4-[5-[4-(7-Ethoxy-8-methyl-2-oxo-2H-2-chromenyl)piperazino]pentyl]oxy]-5-methoxy-2-nitrobenzoyl}pyrrolidine-2-carboxaldehyde diethylthioacetal of formula III (756 mg, 1 mmol) was dissolved in methanol (10 mL) and to this was added SnCl$_2$.2H$_2$O (1.125 g, 5 mmol) and was refluxed for 1.5 h. The reaction mixture was neutralized to pH 8 with NaHCO$_3$ solution and then extracted with ethyl acetate (3×20 ml). The combined organic phase was dried over Na$_2$SO$_4$ and evaporated under reduced pressure to afford the crude (2S)-N-{4-[4-[5-[4-(7-ethoxy-8-methyl-2-oxo-2H-2-chromenyl)piperazino]pentyl]oxy]-5-methoxy-2-aminobenzoyl}pyrrolidine-2-carboxaldehyde diethylthioacetal 4

To a solution of (2S)-N-{4-[4-[5-[4-(7-ethoxy-8-methyl-2-oxo-2H-2-chromenyl)piperazino]pentyl]oxy]-5-methoxy-2-aminobenzoyl}pyrrolidine-2-carboxaldehyde diethylthioacetal of formula 4 (726 mg, 1 mmol), HgCl$_2$ (613 mg, 2.26 mmol) and CaCO$_3$ (246 mg, 2.46 mmol) in CH$_3$CN/H$_2$O (4:1) was stirred at room temperature for 12 h until the completion of the reaction as shown by TLC (EtOAc). The organic layer is evaporated in vacuum and the residue is diluted with EtOAc. To this, saturated NaHCO$_3$ was added slowly at room temperature and the mixture was filtered through a celite bed and washed with ethyl acetate. The filtrate was evaporated in vacuum to get crude 7-methoxy-8-{5-[4-(7-ethoxy-8-methyl-2-oxo-2H-4-chromenyl)piperazino]pentyl}-oxy-(11aS)-1,2,3,11a-5H-pyrrolo[2,1,-c][1,4]benzodiazepin-5-one 5, which was further purified by column chromatography on silica gel eluting first with ethyl acetate to remove traces of mercuric salts and then with CHCl$_3$:methanol (9:1).

H$^1$ NMR (CDCl$_3$, 200 MHz): δ 1.40-1.50 (t, 3H, J=6.75 Hz), 1.70-2.00 (m, 6H), 2.10 (s, 3H), 2.60-2.90 (m, 4H), 3.00-3.15 (m, 4H), 3.40-3.52 (m, 4H), 3.70-3.90 (m, 4H), 3.95 (s, 3H), 4.15-4.20 (m, 5H), 5.60 (s, 1H), 6.78 (s, 1H), 6.80-6.82 (d, 1H, J=9.03 Hz), 7.32-7.45 (d, 1H, J=9.03 Hz), 7.52 (s, 1H), 7.65-7.85 (d, 1H, J=4.50 Hz); MS (FAB) 603 [M+H]$^+$

EXAMPLE 10

To a solution of (2S)-N-[4-(3-bromopropyl)-oxy-5-methoxy-2-nitrobenzoyl]pyrrolidine-2-carboxaldehyde diethylthioacetal of formula 2 (521 mg, 1.0 mmol), 7-isopropoxy-8-methyl-4-piperazino-2H-2-chromenone of formula 1 (302 mg, 1.0 mmol) and K$_2$CO$_3$ (414 mg, 3.0 mmol), in dry acetonitrile (40 ml) was refluxed for 48 hrs. After the completion of the reaction as indicated by TLC, EtOAc:hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[3-[4-(7-isopropoxy-8-methyl-2-oxo-2H-2-chromenyl)piperazino]propyl]oxy]-5-methoxy-2-nitrobenzoyl}pyrrolidine-2-carboxaldehyde diethylthioacetal 3

H$^1$ NMR (CDCl$_3$, 200 MHz): δ 1.20-1.40 (m, 12H), 1.50-2.00 (m, 6H), 2.10-2.40 (m, 5H), 2.60-3.10 (m, 8H), 3.25-3.40 (m, 6H), 3.95 (s, 3H), 4.0-4.2 (m, 2H), 4.25-4.30 (m, 1H), 4.60-4.68 (m, 1H), 4.78-4.80 (m, 1H), 5.65 (s, 1H), 6.68-6.70 (d, 1H, J=9.15 Hz), 6.78 (s, 1H), 7.25-7.35 (d, 1H, J=8.31 Hz), 7.62 (s, 1H) MS (FAB) 743 [M+H]$^+$ (2S)-N-{4-[4-[3-[4-(7-Isopropoxy-8-methyl-2-oxo-2H-2-chromenyl)piperazino]propyl]oxy]-5-methoxy-2-nitrobenzoyl}pyrrolidine-2-carboxaldehyde diethylthioacetal of formula 3 (742 mg, 1 mmol) was dissolved in methanol (10 mL) and to this was added SnCl$_2$.2H$_2$O (1.125 g, 5 mmol) and was refluxed for 1.5 h. The reaction mixture was neutralized to pH 8 with NaHCO$_3$ solution and then extracted with ethyl acetate (3×20 ml). The combined organic phase was dried over Na$_2$SO$_4$ and evaporated under reduced pressure to afford the crude (2S)-N-{4-[4-[3-[4-(7-isopropoxy-8-methyl-2-oxo-2H-2-chromenyl)piperazino]propyl]oxy]-5-methoxy-2-aminobenzoyl}pyrrolidine-2-carboxaldehyde diethylthioacetal 4

To a solution of (2S)-N-{4-[4-[3-[4-(7-isopropoxy-8-methyl-2-oxo-2H-2-chromenyl)piperazino]propyl]oxy]-5-methoxy-2-aminobenzoyl}pyrrolidine-2-carboxaldehyde diethylthioacetal of formula 4 (712 mg, 1 mmol), HgCl$_2$ (613 mg, 2.26 mmol) and CaCO$_3$ (246 mg, 2.46 mmol) in CH$_3$CN/H$_2$O (4:1) was stirred at room temperature for 12 h until the completion of the reaction as shown by TLC (EtOAc). The organic layer is evaporated in vacuum and the residue is diluted with EtOAc. To this, saturated NaHCO$_3$ was added slowly at room temperature and the mixture was filtered through a celite bed and washed with ethyl acetate. The filtrate was evaporated in vacuum to get crude 7-methoxy-8-{3-[4-(7-isopropoxy-8-methyl-2-oxo-2H-4-chromenyl) piperazino]propyl}-oxy-(11aS)-1,2,3,11a-5H-pyrrolo[2,1-c][1,4]benzodiazepin-5-one 5, which was further purified by column chromatography on silica gel eluting first with ethyl acetate to remove traces of mercuric salts and then with CHCl$_3$:methanol (9:1).

H$^1$ NMR (CDCl$_3$, 200 MHz): δ 1.40-1.50 (d, 6H, J=7.61 Hz), 1.65-2.10 (m, 4H), 2.15 (s, 3H), 2.61-2.80 (m, 4H), 3.0-3.15 (m, 4H), 3.40-3.55 (m, 4H), 3.95 (s, 3H), 4.0-4.2 (m, 6H), 5.65 (s, 1H), 6.68-6.70 (d, 1H, J=9.15 Hz), 6.78 (s, 1H), 7.25-7.35 (d, 1H, J=8.31 Hz), 7.62 (s, 1H), 7.64-7.74 (d, 1H, J=3.70 Hz) MS (FAB) 589 [M+H]$^+$

EXAMPLE 11

To a solution of (2S)-N-[4-(4-bromobutyl)-oxy-5-methoxy-2-nitrobenzoyl]pyrrolidine-2-carboxaldehyde diethylthioacetal of formula 2 (535 mg, 1.0 mmol), 7-isopropoxy-8-methyl-4-piperazino-2H-2-chromenone of formula 1 (302 mg, 1.0 mmol) and K$_2$CO$_3$ (414 mg, 3.0 mmol), in dry acetonitrile (40 ml) was refluxed for 48 hrs. After the completion of the reaction as indicated by TLC, EtOAc:hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[4-[4-(7-isopropoxy-8-methyl-2-oxo-2H-2-chromenyl)piperazino]butyl]oxy]-5-methoxy-2-nitrobenzoyl}pyrrolidine-2-carboxaldehyde diethylthioacetal 3

H$^1$ NMR (CDCl$_3$, 200 MHz): δ 1.20-1.40 (m, 12H), 1.50-2.00 (m, 8H), 2.10-2.40 (m, 5H), 2.60-3.10 (m, 8H), 3.25-3.40 (m, 6H), 3.95 (s, 3H), 4.0-4.2 (m, 2H), 4.25-4.30 (m, 1H), 4.60-4.68 (m, 1H), 4.78-4.80 (m, 1H), 5.65 (s, 1H), 6.68-6.70 (d, 1H, J=9.15 Hz), 6.78 (s, 1H), 7.25-7.35 (d, 1H, J=8.31 Hz), 7.62 (s, 1H) MS (FAB) 757 [M+H]$^+$ (2S)-N-{4-[4-[4-[4-(7-Isopropoxy-8-methyl-2-oxo-2H-2-chromenyl)piperazino]butyl]oxy]-5-methoxy-2-nitrobenzoyl}pyrrolidine-2-carboxaldehyde diethylthioacetal of formula 3 (756 mg, 1 mmol) was dissolved in methanol (10 mL) and to this was added SnCl$_2$.2H$_2$O (1.125 g, 5 mmol) and was refluxed for 1.5 h. The reaction mixture was neutralized to pH 8 with NaHCO$_3$ solution and then extracted with ethyl acetate (3×20 ml). The combined organic phase was dried over Na$_2$SO$_4$ and evaporated under reduced pressure to afford the crude (2S)-N-{4-[4-[4-[4-(7-isopropoxy-8-methyl-2-oxo-2H-2-chromenyl)piperazino]butyl]oxy]-5-methoxy-2-aminobenzoyl}pyrrolidine-2-carboxaldehyde diethylthioacetal 4

To a solution of (2S)-N-{4-[4-[4-[4-(7-isopropoxy-8-methyl-2-oxo-2H-2-chromenyl)piperazino]butyl]oxy]-5-methoxy-2-aminobenzoyl}pyrrolidine-2-carboxaldehyde diethylthioacetal of formula 4 (726 mg, 1 mmol), HgCl$_2$ (613 mg, 2.26 mmol) and CaCO$_3$ (246 mg, 2.46 mmol) in CH$_3$CN/H$_2$O (4:1) was stirred at room temperature for 12 h until the completion of the reaction as shown by TLC (EtOAc). The organic layer is evaporated in vacuum and the residue is diluted with EtOAc. To this, saturated NaHCO$_3$ was added slowly at room temperature and the mixture was filtered through a celite bed and washed with ethyl acetate. The filtrate was evaporated in vacuum to get crude 7-methoxy-8-{4-[4-(7-isopropoxy-8-methyl-2-oxo-2H-4-chromenyl) piperazino]butyl}-oxy-(11aS)-1,2,3,11a-5H-pyrrolo[2,1-c][1,4]benzodiazepin-5-one 5, which was further purified by column chromatography on silica gel eluting first with ethyl acetate to remove traces of mercuric salts and then with CHCl$_3$:methanol (9:1).

H$^1$ NMR (CDCl$_3$, 200 MHz): δ 1.40-1.50 (d, 6H, J=6.10 Hz), 1.65-2.10 (m, 6H), 2.15 (s, 3H), 2.61-2.80 (m, 4H), 3.0-3.15 (m, 4H), 3.40-3.55 (m, 4H), 3.95 (s, 3H), 4.0-4.2 (m, 6H), 5.65 (s, 1H), 6.68-6.70 (d, 1H, J=9.15 Hz), 6.78 (s, 1H), 7.25-7.35 (d, 1H, J=8.31 Hz), 7.62 (s, 1H), 7.64-7.74 (d, 1H, J=3.70 Hz); MS (FAB) 603 [M+H]$^+$

EXAMPLE 12

To a solution of (2S)-N-[4-(5-bromopentyl)-oxy-5-methoxy-2-nitrobenzoyl]pyrrolidine-2-carboxaldehyde diethylthioacetal of formula 2 (549 mg, 1.0 mmol), 7-isopropoxy-8-methyl-4-piperazino-2H-2-chromenone of formula 1 (302 mg, 1.0 mmol) and K$_2$CO$_3$ (414 mg, 3.0 mmol), in dry acetonitrile (40 ml) was refluxed for 48 hrs. After the completion of the reaction as indicated by TLC, EtOAc:hexane (1:1), the reaction mixture was poured on to the water and then extracted with ethyl acetate. This was concentrated under reduced pressure gave the crude product which was further purified by column chromatography on silica gel eluting with EtOAc:hexane (3:7) to give the pure (2S)-N-{4-[4-[5-[4-(7-isopropoxy-8-methyl-2-oxo-2H-2-chromenyl)piperazino]pentyl]oxy]-5-methoxy-2-nitrobenzoyl}pyrrolidine-2-carboxaldehyde diethylthioacetal 3

H$^1$ NMR (CDCl$_3$, 200 MHz): δ 1.20-1.40 (m, 14H), 1.50-2.00 (m, 8H), 2.10-2.40 (m, 5H), 2.61-3.10 (m, 8H), 3.20-3.40 (m, 6H), 3.95 (s, 3H), 4.0-4.2 (m, 2H), 4.25-4.30 (m, 1H), 4.60-4.70 (m, 1H), 4.80-4.83 (m, 1H), 5.65 (s, 1H), 6.68-6.70 (d, 1H, J=9.15 Hz), 6.78 (s, 1H), 7.25-7.35 (d, 1H, J=8.31 Hz), 7.62 (s, 1H) MS (FAB) 771 [M+H]$^+$ (2S)-N-{4-[4-[5-[4-(7-Iisopropoxy-8-methyl-2-oxo-2H-2-chromenyl)piperazino]pentyl]oxy]-5-methoxy-2-nitrobenzoyl}pyrrolidine-2-carboxaldehyde diethylthioacetal of formula 3 (770 mg, 1 mmol) was dissolved in methanol (10 mL) and to this was added SnCl$_2$.2H$_2$O (1.125 g, 5 mmol) and was refluxed for 1.5 h. The reaction mixture was neutralized to pH 8 with NaHCO$_3$ solution and then extracted with ethyl acetate (3×20 ml). The combined organic phase was dried over Na$_2$SO$_4$ and evaporated under reduced pressure to afford the crude (2S)-N-{4-[4-[5-[4-(7-isopropoxy-8-methyl-2-oxo-2H-2-chromenyl)piperazino] pentyl]oxy]-5-methoxy-2-aminobenzoyl}pyrrolidine-2-carboxaldehyde diethylthioacetal 4

To a solution of (2S)-N-{4-[4-[5-[4-(7-isopropoxy-8-methyl-2-oxo-2H-2-chromenyl)piperazino]pentyl]oxy]-5-methoxy-2-aminobenzoyl}pyrrolidine-2-carboxaldehyde diethylthioacetal of formula 4 (740 mg, 1 mmol), HgCl$_2$ (613 mg, 2.26 mmol) and CaCO$_3$ (246 mg, 2.46 mmol) in CH$_3$CN/H$_2$O (4:1) was stirred at room temperature for 12 h until the completion of the reaction as shown by TLC (EtOAc). The organic layer is evaporated in vacuum and the residue is diluted with EtOAc. To this, saturated NaHCO$_3$ was added slowly at room temperature and the mixture was filtered through a celite bed and washed with ethyl acetate. The filtrate was evaporated in vacuum to get crude 7-methoxy-8-{5-[4-(7-isopropoxy-8-methyl-2-oxo-2H-4-chromenyl) piperazino]pentyl}-oxy-(11aS)-1,2,3,11a-5H-pyrrolo[2,1-c][1,4]benzodiazepin-5-one 5, which was further purified by column chromatography on silica gel eluting first with ethyl acetate to remove traces of mercuric salts and then with CHCl$_3$:methanol (9:1).

H$^1$ NMR (CDCl$_3$, 200 MHz): δ 1.40-1.50 (d, 6H, J=6.53 Hz), 1.65-2.10 (m, 8H), 2.15 (s, 3H), 2.61-2.80 (m, 4H), 3.0-3.15 (m, 4H), 3.40-3.55 (m, 4H), 3.95 (s, 3H), 4.0-4.2 (m, 6H), 5.65 (s, 1H), 6.68-6.70 (d, 1H, J=9.15 Hz), 6.78 (s, 1H), 7.25-7.35 (d, 1H, J=8.31 Hz), 7.62 (s, 1H), 7.64-7.74 (d, 1H, J=3.70 Hz) MS (FAB) 617 [M+H]$^+$

Biological Activity: In vitro biological activity studies were carried out at the National Cancer Institute (USA).

Cytotoxicity: The compounds 7-methoxy-8-{5-[4-(2-oxo-2H-4-chromenyl)piperazino]pentyl}-oxy-(11aS)-1,2,3,11a-5H-pyrrolo[2,1-c][1,4]benzodiazepin-5-one, 7-methoxy-8-{3-[4-(7-methoxy-8-methyl-2-oxo-2H-4-chromenyl) piperazino]propyl}-oxy-(11aS)-1,2,3,11a-5H-pyrrolo[2,1-c][1,4]benzodiazepin-5-one and 7-methoxy-8-{5-[4-(7-methoxy-8-methyl-2-oxo-2H-4-chromenyl)piperazino] pentyl}-oxy-(11aS)-1,2,3,11a-5H-pyrrolo[2,1-c][1,4] benzodiazepin-5-one were evaluated for in vitro anticancer activity against sixty human tumor cells derived from nine cancer types (leukemia, non-small-cell lung, colon, CNS, melanoma, ovarian, prostate, and breast cancer) as shown in (Table 2). For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of log$_{10}$ TGI and log$_{10}$ LC50 as well as log$_{10}$ GI50 for 5c, 5d and 5f are listed in Table 1. As demonstrated by mean graph pattern, compound 5c exhibits an interesting profile of activity and selectivity for various cell lines. The mean graph mid point of log$_{10}$ TGI and log$_{10}$ LC50 showed similar pattern to the log$_{10}$ GI50 mean graph mid points.

TABLE 1

Log$_{10}$GI50 log$_{10}$TGI and log$_{10}$LC50 mean graphs midpoints (MG_MID) of in vitro cytotoxicity data for the representative compounds against human tumor cell lines

| Compound | Log$_{10}$GI50 | Log$_{10}$TGI | Log$_{10}$LC50 |
|---|---|---|---|
| 5c | −7.68 | −6.66 | −4.99 |
| 5d | −5.68 | −4.86 | −4.19 |
| 5f | −6.49 | −5.85 | −4.96 |

TABLE 2

Log$_{10}$LC50 concentration in mol/L causing 50% lethality values for the representative compounds

| Cancer | Compound 5c | Compound 5d | Compound 5f |
|---|---|---|---|
| Leukemia | −5.03 | −4.22 | −5.39 |
| Non-small-cell-lung | −4.92 | −4.23 | −4.87 |
| Colon | −5.24 | −4.87 | −5.41 |
| CNS | −4.70 | −4.11 | −4.63 |
| Melanoma | −5.68 | −4.34 | −5.29 |
| Ovarian | −5.44 | −4.00 | −4.28 |
| Renal | −5.26 | −5.29 | −5.17 |
| Prostate | −4.53 | −4.00 | −4.85 |
| Breast | −4.71 | −4.11 | −4.52 |

Each cancer type represents the average of six to nine different cancer cell lines.

The invention claimed is:

1. A compound of formula 5:

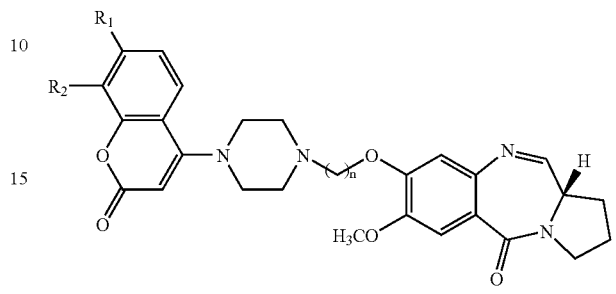

wherein R$_1$ is H or alkoxy group selected from methoxy, ethoxy and propoxy groups, R$_2$ is H or CH$_3$ and n is an integer varying from 3-5.

2. The compound of claim 1 wherein the compound is selected from:
   7-Methoxy-8-{3-[4-(2-oxo-2H-4-chromenyl)piperazino] propyl}-oxy-(11aS)-1,2,3,11a-5H-pyrrolo[2,1-c][1,4] benzodiazepin-5-one(5a),
   7-Methoxy-8-{4-[4-(2-oxo-2H-4-chromenyl)piperazino] butyl}-oxy-(11aS)-1,2,3,11a-5H-pyrrolo[2,1-c][1,4] benzodiaze pin-5-one(5b),
   7-Methoxy-8-{5-[4-(2-oxo-2H-4-chromenyl)piperazino] pentyl}-oxy-(11aS)-1,2,3,11a-5H-pyrrolo[2,1-c][1,4] benzodiazepin-5-one(5c),
   7-Methoxy-8-{3-[4-(7-methoxy-8-methyl-2-oxo-2H-4-chromenyl)piperazino]propyl}-oxy-(11aS)-1,2,3,11a-5H-pyrrolo[2,1-c][1,4]benzodiazepin-5-one(5d),
   7-Methoxy-8-{4-[4-(7-methoxy-8-methyl-2-oxo-2H-4-chromenyl)piperazino]butyl}-oxy-(11aS)-1,2,3,11a-5H-pyrrolo[2,1-c][1,4]benzodiazepin-5-one(5e),
   7-Methoxy-8-{5-[4-(7-methoxy-8-methyl-2-oxo-2H-4-chromenyl)piperazino]pentyl}-oxy-(11aS)-1,2,3,11a-5H-pyrrolo[2,1-c][1,4]benzodiazepin-5-one(5f),
   7-Methoxy-8-{3-[4-(7-ethoxy-8-methyl-2-oxo-2H-4-chromenyl) piperazino]propyl}-oxy-(11aS)-1,2,3,11a-5H-pyrrolo[2,1-c][1,4]benzodiazepin-5-one (5g),
   7-Methoxy-8-{4-[4-(7-ethoxy-8-methyl-2-oxo-2H-4-chromenyl)piperazino]butyl}-oxy}-(11aS)-1,2,3,11a-5H-pyrrolo[2,1-c][1,4]benzodiazepin-5-one(5b),
   7-Methoxy-8-{5-[4-(7-ethoxy-8-methyl-2-oxo-2H-4-chromenyl)piperazino]pentyl}-oxy-(11a S)-1,2,3,11a-5H-pyrrolo[2,1-c][1,4]benzodiazepin-5-one(5i),
   7-Methoxy-8-{3-[4-(7-isopropoxy-8-methyl-2-oxo-2H-4-chromenyl)piperazino]propyl}-oxy-(11aS)-1,2,3, 11a-5H-pyrrolo[2,1-c][1,4]benzodiazepin-5-one(5j),
   7-Methoxy-8-{4-[4-(7-isopropoxy-8-methyl-2-oxo-2H-4-chromenyl)piperazino]butyl}-oxy-(11aS)-1,2,3,11a-5H-pyrrolo[2,1-c][1,4]benzodiazepin-5-one(5k),
   7-Methoxy-8-{5-[4-(7-isopropoxy-8-methyl-2-oxo-2H-4-chromenyl)piperazino]pentyl}-oxy-(11aS)-1,2,3, 11a-5H-pyrrolo[2,1-c][1,4]benzodiazepin-5-one(5l).

3. A pharmaceutical composition comprising a compound of claim 1, or its pharmaceutically acceptable salt and one or more pharmaceutically acceptable carriers.

4. The pharmaceutical composition of claim 3, wherein the compound of claim 1 has the structure of formula 5

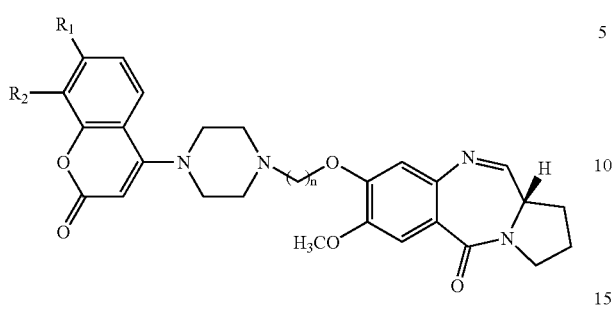

wherein $R_1$ is selected from methoxy, ethoxy and propoxy groups, $R_2$ is H or $CH_3$ and n is an integer varying from 3-5.

5. A process for the preparation of a compound of formula 5

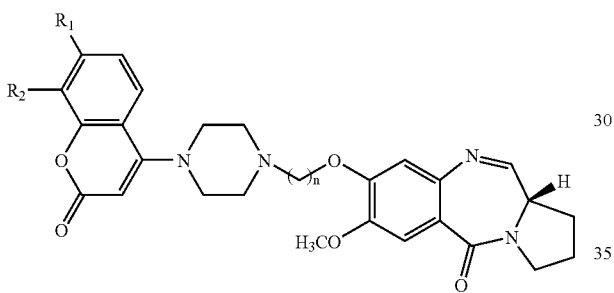

wherein $R_1$ is H or alkoxy group selected from methoxy, ethoxy and propoxy groups, $R_2$ is H or $CH_3$ and n is an integer varying from 3-5, the process comprising the steps of:

a) reacting 4-piperazino-2H-2-chromenone or 7-alkoxy-8-methyl-4-piperazino-2H-2-chromenone of formula 1

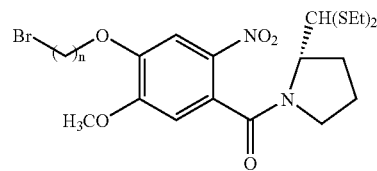

wherein $R_1$ is H or alkoxy group selected from methoxy, ethoxy and propoxy groups, $R_2$ is H or $CH_3$ and n is an integer from 3-5 with (2S)-N-[4-(n-bromoalkyl)-oxy-5-methoxy-2-nitrobenzoyl]pyrrolidine-2-carboxaldehyde diethylthioacetal of formula 2

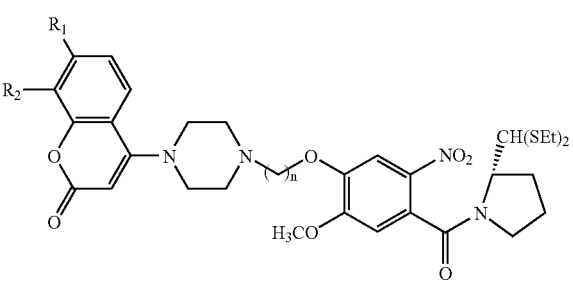

in the presence of a base, in a dry organic solvent, for a period of about 48 hours under reflux, followed by extraction in water and isolating the compound of (2S)-N-{4-[4-[n-[4-(2-oxo-2H-2-chromenyl)piperazino]alkyl]oxy]-5-methoxy-2-nitrobenzoyl}pyrrolidine-2-carboxaldehyde diethylthioacetal or (2S)-N-{4-[4-[n-[4-(7-alkyloxy-8-methyl-2-oxo-2H-2-chromenyl)piperazino]alkyl]oxy]-5-methoxy-2-nitrobenzoyl}pyrrolidine-2-carboxaldehyde diethylthioacetal of formula 3,

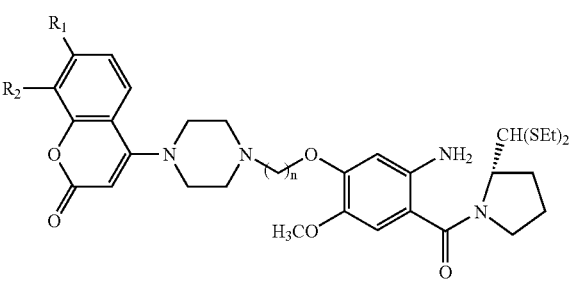

wherein $R_1$ is H or alkoxy group selected from methoxy, ethoxy and propoxy groups, $R_2$ is H or $CH_3$ and n is an integer varying from 3-5, b) reducing the nitro compound of formula 3 with $SnCl_2.2H_2O$ or an acid catalyst in the presence of an organic solvent, under reflux, for a period of about 1-2 hrs, followed by neutralizing the resultant reaction mixture at a pH of about 8 and isolating the amino compound (2S)-N-{4-[4-[n-[4-(2-oxo-2H-2-chromenyl)piperazino]alkyl]oxy]-5-methoxy-2-aminobenzoyl}pyrrolidine-2-carboxaldehyde diethylthioacetal or (2S)-N-{4-[4-[n-[4-(7-methoxy-8-methyl-2-oxo-2H-2-chromenyl)piperazino]alkyl]oxy]-5-methoxy-2-aminobenzoyl}pyrrolidine-2-carboxaldehyde diethylthioacetal of formula 4, wherein $R_1$ is H or alkoxy group selected from methoxy, ethoxy and propoxy groups, $R_2$ is H or $CH_3$ and n is an integer varying from 3-5, c) reacting the amino compound of formula 4 with a deprotecting agent in the presence of an aqueous organic solvent, at a temperature from about 20 to about 25° C., for a period of about 12 hrs, separating the organic layer from the resultant reaction mixture followed by evaporation under vacuum to obtain the residue and diluting the above said residue with ethyl acetate followed by mixing with saturated sodium bicarbonate, filtering, washing and evaporating the resultant filtrate, followed by purification to obtain the desired pyrrolo[2,1-c][1,4]benzodiazepine hybrid of formula 5.

6. The process of claim 5, wherein the base used in step (a) is selected from $K_2CO_3$ and $Na_2CO_3$.

7. The process of claim 5, wherein the organic solvent used in step (a) is selected from acetonitrile, acetone and N,N-dimethyl formamide.

8. The process of claim 5, wherein the acid catalyst used in step (b) is selected from the group consisting of Sn/HCl, Zn/$CH_3$COOH and Pd/C—$H_2$.

9. The process of claim 5, wherein the organic solvent used in step (b) is an alcohol selected from the group consisting of methanol, ethanol and ethyl acetate.

10. The process of claim 5, wherein the de-protecting agent used in step (c) is selected from the group consisting of $HgCl_2$/$CaCO_3$, HgO/HgCl$[2]_2$ and Bi(OTf)$_3$.x$H_2O$.

11. The process of claim 5, wherein the organic solvent used in step (c) is selected from the group consisting of acetonitrile, dichloromethane and chloroform.

12. The process of claim 5, wherein the compound obtained is selected from:

7-Methoxy-8-{3-[4-(2-oxo-2H-4-chromenyl)piperazino]propyl}-oxy-(11aS)-1,2,3,11a-5H-pyrrolo[2,1-c][1,4]benzodiazepin-5-one(5a), 7-Methoxy-8-{4-[4-(2-oxo-2H-4-chromenyl)piperazino]butyl}-oxy-(11aS)-1,2,3,11a-5H-pyrrolo[2,1-c][1,4]benzodiazepin-5-one(5b), 7-Methoxy-8-{5-[4-(2-oxo-2H-4-chromenyl)piperazino]pentyl}-oxy-(11aS)-1,2,3,11a-5H-pyrrolo[2,1-c][1,4]benzodiazepin-5-one(5c), 7-Methoxy-8-{3-[4-(7-methoxy-8-methyl-2-oxo-2H-4-chromenyl)piperazino]propyl}-oxy-(11aS)-1,2,3,11a-5H-pyrrolo[2,1-c][1,4]benzodiazepin-5-one(5d), 7-Methoxy-8-{4-[4-(7-methoxy-8-methyl-2-oxo-2H-4-chromenyl)piperazino]butyl}-oxy-(11aS)-1,2,3,11a-5H-pyrrolo[2,1-c][1,4]benzodiazepin-5-one(5e), 7-Methoxy-8-{5-[4-(7-methoxy-8-methyl-2-oxo-2H-4-chromenyl)piperazino]pentyl}-oxy-(11aS)-1,2,3,11a-5H-pyrrolo[2,1-c][1,4]benzodiazepin-5-one(5f), 7-Methoxy-8-{3-[4-(7-ethoxy-8-methyl-2-oxo-2H-4-chromenyl)piperazino]propyl}-oxy-(11aS)-1,2,3,11a-5H-pyrrolo[2,1-c][1,4]benzodiazepin-5-one(5g), 7-Methoxy-8-{4-[4-(7-ethoxy-8-methyl-2-oxo-2H-4-chromenyl)piperazino]butyl}-oxy}-(11aS)-1,2,3,11a-5H-pyrrolo[2,1-c][1,4]benzodiazepin-5-one(5h), 7-Methoxy-8-{5-[4-(7-ethoxy-8-methyl-2-oxo-2H-4-chromenyl)piperazino]pentyl}-oxy-(11aS)-1,2,3,11a-5H-pyrrolo[2,1-c][1,4]benzodiazepin-5-one(5i), 7-Methoxy-8-{3-[4-(7-isopropoxy-8-methyl-2-oxo-2H-4-chromenyl)piperazino]propyl}-oxy-(11aS)-1,2,3,11a-5H-pyrrolo[2,1-c][1,4]benzodiazepine-5-one(5j), 7-Methoxy-8-{4-[4-(7-isopropoxy-8-methyl-2-oxo-2H-4-chromenyl)piperazino]butyl}-oxy-(11aS)-1,2,3,11a-5H-pyrrolo[2,1-c][1,4]benzodiazepin-5-one(5k), and 7-Methoxy-8-{5-[4-(7-isopropoxy-8-methyl-2-oxo-2H-4-chromenyl)piperazino]pentyl}-oxy-(11aS)-1,2,3,11a-5H-pyrrolo[2,1-c][1,4]benzodiazepin-5-one(5l).

\* \* \* \* \*

UNITED STATES PATENT AND TRADEMARK OFFICE
CERTIFICATE OF CORRECTION

PATENT NO.      : 7,312,210 B2
APPLICATION NO. : 11/367223
DATED           : December 25, 2007
INVENTOR(S)     : Kamal et al.

It is certified that error appears in the above-identified patent and that said Letters Patent is hereby corrected as shown below:

On Title page (Other Publications), Col. 2, line 1, please delete "synethesis," and insert --synthesis,--, therefor.

On Title page (Other Publications), Col. 2, line 12, please delete "mitromycin" and insert --mitomycin--, therefor.

On Title page (Abstract), Col. 2, line 11, after "[1,4]" please delete ". benzodiazepine" and insert --benzodiazepin--, therefor.

Drawing–On sheet 1 of 1 (below Structure 3) (Scheme--1), line 3 (approx.), please delete "$SnCl_2.2H_2O$" and insert --$SnCl_2 \cdot 2H_2O$--, therefor.

In Col. 1, line 27, please delete "benzodiazepine" and insert --benzodiazepin--, therefor.

In Col. 2, line 14 (approx.), please delete "amthramycin" and insert --anthramycin--, therefor.

In Col. 2, line 46 (approx.), please delete "C2" and insert --$C_2$--, therefor.

In Col. 3, line 46, after "oxy" please delete "}".

In Col. 3, line 67, please delete "antitumoric" and insert --antitumor--, therefor.

In Col. 5, line 63, please delete "$SnCl_2.2H_2O$" and insert --$SnCl_2 \cdot 2H_2O$--, therefor.

In Col. 6, line 40, please delete "demethyl" and insert --dimethyl--, therefor.

In Col. 6, line 49, please delete "$Bi(OTf)_3.xH_2O$." and insert --$Bi(OTf)_3 \cdot xH_2O$.--, therefor.

In Col. 7, line 9, after "oxy" please delete "}".

In Col. 7, line 16, please delete "benzodiazepine" and insert --benzodiazepin--, therefor.

UNITED STATES PATENT AND TRADEMARK OFFICE
CERTIFICATE OF CORRECTION

PATENT NO. : 7,312,210 B2
APPLICATION NO. : 11/367223
DATED : December 25, 2007
INVENTOR(S) : Kamal et al.

It is certified that error appears in the above-identified patent and that said Letters Patent is hereby corrected as shown below:

In Col. 8, line 4, please delete "CDCl$_3$," and insert --CdCl$_3$,--, therefor.

In Col. 8, line 11, please delete "Oxo" and insert --oxo--, therefor.

In Col. 8, line 15 (approx.), please delete "SnCl$_2$.2H$_2$O" and insert --SnCl$_2$•2H$_2$O--, therefor.

In Col. 8, line 24 (approx.), after "4" please insert --.--.

In Col. 8, line 42 (approx.), please delete "CDCl$_3$," and insert --CdCl$_3$,--, therefor.

In Col. 9, line 1, please delete "CDCl$_3$," and insert --CdCl$_3$,--, therefor.

In Col. 9, line 8, please delete "Oxo" and insert --oxo--, therefor.

In Col. 9, line 12, please delete "SnCl$_2$.2H$_2$O" and insert --SnCl$_2$•2H$_2$O--, therefor.

In Col. 9, line 19, after "4" please insert --.--.

In Col. 9, line 38, please delete "CDCl$_3$," and insert --CdCl$_3$,--, therefor.

In Col. 9, line 63, please delete "CDCl$_3$," and insert --CdCl$_3$,--, therefor.

In Col. 10, line 3, please delete "Oxo" and insert --oxo--, therefor.

In Col. 10, line 8 (approx.), please delete "SnCl$_2$.2H$_2$O" and insert --SnCl$_2$•2H$_2$O--, therefor.

In Col. 10, line 15, after "4" please insert --.--.

In Col. 10, line 34 (approx.), please delete "CDCl$_3$," and insert --CdCl$_3$,--, therefor.

In Col. 10, line 61, please delete "CDCl$_3$," and insert --CdCl$_3$,--, therefor.

UNITED STATES PATENT AND TRADEMARK OFFICE
CERTIFICATE OF CORRECTION

PATENT NO.        : 7,312,210 B2
APPLICATION NO.   : 11/367223
DATED             : December 25, 2007
INVENTOR(S)       : Kamal et al.

It is certified that error appears in the above-identified patent and that said Letters Patent is hereby corrected as shown below:

In Col. 11, line 5, please delete "$SnCl_2.2H_2O$" and insert --$SnCl_2 \cdot 2H_2O$--, therefor.

In Col. 11, line 13, after "4" please insert --.--.

In Col. 11, line 32, please delete "$CDCl_3$," and insert --$CdCl_3$,--, therefor.

In Col. 11, line 32, please delete "Hz))," and insert --Hz),--, therefor.

In Col. 11, line 37, please delete "[M+H]+" and insert --$[M+H]^+$--, therefor.

In Col. 11, line 57, please delete "$CDCl_3$," and insert --$CdCl_3$,--, therefor.

In Col. 11, line 67, please delete "$SnCl_2.2H_2O$" and insert --$SnCl_2 \cdot 2H_2O$--, therefor.

In Col. 12, line 8, after "4" please insert --.--.

In Col. 12, Line 27, please delete "$CDCl_3$," and insert --$CdCl_3$,--, therefor.

In Col. 12, line 30, please delete "Hz))," and insert --Hz),--, therefor.

In Col. 12, line 49, please delete "piperzino]" and insert --piperazino]--, therefor.

In Col. 12, line 52, please delete "$CDCl_3$," and insert --$CdCl_3$,--, therefor.

In Col. 12, line 64, please delete "$SnCl_2.2H_2O$" and insert --$SnCl_2 \cdot 2H_2O$--, therefor.

In Col. 13, line 5, after "4" please insert --.--.

In Col. 13, line 25, please delete "$CDCl_3$," and insert --$CdCl_3$,--, therefor.

In Col. 13, line 28, please delete "Hz))," and insert --Hz),--, therefor.

In Col. 13, line 50, please delete "$CDCl_3$," and insert --$CdCl_3$,--, therefor.

UNITED STATES PATENT AND TRADEMARK OFFICE
CERTIFICATE OF CORRECTION

| | |
|---|---|
| PATENT NO. | : 7,312,210 B2 |
| APPLICATION NO. | : 11/367223 |
| DATED | : December 25, 2007 |
| INVENTOR(S) | : Kamal et al. |

It is certified that error appears in the above-identified patent and that said Letters Patent is hereby corrected as shown below:

In Col. 13, line 57, please delete "Ethoxy" and insert --ethoxy--, therefor.

In Col. 13, line 61, please delete "$SnCl_2.2H_2O$" and insert --$SnCl_2 \cdot 2H_2O$--, therefor.

In Col. 14, line 2, after "4" please insert --.--.

In Col. 14, line 21, please delete "$CDCl_3$," and insert --$CdCl_3$,--, therefor.

In Col. 14, line 48 (approx.), please delete "$CDCl_3$," and insert --$CdCl_3$,--, therefor.

In Col. 14, line 55, please delete "Ethoxy" and insert --ethoxy--, therefor.

In Col. 14, line 59, please delete "$SnCl_2.2H_2O$" and insert --$SnCl_2 \cdot 2H_2O$--, therefor.

In Col. 14, line 67, after "4" please insert --.--.

In Col. 15, line 14, after "oxy" please delete "}".

In Col. 15, line 19, please delete "$CDCl_3$," and insert --$CdCl_3$,--, therefor.

In Col. 15, line 45, please delete "$CDCl_3$," and insert --$CdCl_3$,--, therefor.

In Col. 15, line 49, please delete "05.59" and insert --5.59--, therefor.

In Col. 15, line 52, please delete "Ethoxy" and insert --ethoxy--, therefor.

In Col. 15, line 56, please delete "$SnCl_2.2H_2O$" and insert --$SnCl_2 \cdot 2H_2O$--, therefor.

In Col. 15, line 64, after "4" please insert --.--.

In Col. 16, line 16, please delete "$CDCl_3$," and insert --$CdCl_3$,--, therefor.

UNITED STATES PATENT AND TRADEMARK OFFICE
CERTIFICATE OF CORRECTION

PATENT NO.       : 7,312,210 B2
APPLICATION NO.  : 11/367223
DATED            : December 25, 2007
INVENTOR(S)      : Kamal et al.

It is certified that error appears in the above-identified patent and that said Letters Patent is hereby corrected as shown below:

In Col. 16, line 42, please delete "$CDCl_3$," and insert --$CdCl_3$,--, therefor.

In Col. 16, line 48, please delete "Isopropoxy" and insert --isopropoxy--, therefor.

In Col. 16, line 52, please delete "$SnCl_2.2H_2O$" and insert --$SnCl_2 \cdot 2H_2O$--, therefor.

In Col. 16, line 60, after "4" please insert --.--.

In Col. 17, line 12, please delete "$CDCl_3$," and insert --$CdCl_3$,--, therefor.

In Col. 17, line 25, please delete "$K_2\ CO_3$" and insert --$K_2CO_3$--, therefor.

In Col. 17, line 37, please delete "$CDCl_3$," and insert --$CdCl_3$,--, therefor.

In Col. 17, line 43, please delete "Isopropoxy" and insert --isopropoxy--, therefor.

In Col. 17, line 47, please delete "$SnCl_2.2H_2O$" and insert --$SnCl_2 \cdot 2H_2O$--, therefor.

In Col. 17, line 55, after "4" please insert --.--.

In Col. 18, line 7, please delete "$CDCl_3$," and insert --$CdCl_3$,--, therefor.

In Col. 18, line 34 (approx.), please delete "$CDCl_3$," and insert --$CdCl_3$,--, therefor.

In Col. 18, line 40, please delete "Iisopropoxy" and insert --isopropoxy--, therefor.

In Col. 18, line 44, please delete "$SnCl_2.2H_2O$" and insert --$SnCl_2 \cdot 2H_2O$--, therefor.

In Col. 18, line 52, after "4" please insert --.--.

UNITED STATES PATENT AND TRADEMARK OFFICE
CERTIFICATE OF CORRECTION

PATENT NO. : 7,312,210 B2
APPLICATION NO. : 11/367223
DATED : December 25, 2007
INVENTOR(S) : Kamal et al.

It is certified that error appears in the above-identified patent and that said Letters Patent is hereby corrected as shown below:

In Col. 19, line 4, please delete "$CDCl_3$," and insert --$CdCl_3$,--, therefor.

In Col. 20, line 28 (approx.), Claim 2, please delete "one(5a)," and insert --one (5a),--, therefor.

In Col. 20, line 31 (approx.), Claim 2, please delete "benzodiaze pin" and insert --benzodiazepin--, therefor.

In Col. 20, line 31 (approx.), Claim 2, please delete "one(5b)," and insert --one (5b),--, therefor.

In Col. 20, line 34 (approx.), Claim 2, please delete "one(5c)," and insert --one (5c),--, therefor.

In Col. 20, line 37 (approx.), Claim 2, please delete "one(5d)," and insert --one (5d),--, therefor.

In Col. 20, line 40 (approx.), Claim 2, please delete "one(5e)," and insert --one (5e),--, therefor.

In Col. 20, line 43 (approx.), Claim 2, please delete "one(5f)," and insert --one (5f),--, therefor.

In Col. 20, line 45 (approx.), Claim 2, please delete "chromenyl) piperazino" and insert --chromenyl)piperazino--, therefor.

In Col. 20, line 48 (approx.), Claim 2, please delete "oxy }" and insert --oxy--, therefor.

In Col. 20, line 49 (approx.), Claim 2, please delete "one(5b)," and insert --one (5h),--, therefor.

In Col. 20, line 51 (approx.), Claim 2, please delete "(11a S)" and insert --(11aS)--, therefor.

In Col. 20, line 52 (approx.), Claim 2, please delete "one(5i)," and insert --one (5i),--, therefor.

UNITED STATES PATENT AND TRADEMARK OFFICE
CERTIFICATE OF CORRECTION

PATENT NO. : 7,312,210 B2
APPLICATION NO. : 11/367223
DATED : December 25, 2007
INVENTOR(S) : Kamal et al.

It is certified that error appears in the above-identified patent and that said Letters Patent is hereby corrected as shown below:

In Col. 20, line 56 (approx.), Claim 2, please delete "one(5j)," and insert --one (5j),--, therefor.

In Col. 20, line 59 (approx.), Claim 2, please delete "one(5k)," and insert --one (5k),--, therefor.

In Col. 20, line 62 (approx.), Claim 2, please delete "one(5l)," and insert --one (5l),--, therefor.

In Col. 22, line 41 Claim 5, please delete "$SnCl_2.2H_2O$" and insert --$SnCl_2 \cdot 2H_2O$--, therefor.

In Col. 23, line 29, Claim 10, please delete "$HgO/HgCl[2]_2$" and insert --$HgO/HgCl_2$--, therefor.

In Col. 23, line 29, Claim 10, please delete "$Bi(Otf)_3.xH_2O$" and insert --$Bi(Otf)_3 \cdot xH_2O$--, therefor.

In Col. 23, line 37, Claim 12, please delete "one(5a)," and insert --one (5a),--, therefor.

In Col. 24, line 3, Claim 12, please delete "one(5b)," and insert --one (5b),--, therefor.

In Col. 24, line 6 (approx.), Claim 12, please delete "one(5c)," and insert --one (5c),--, therefor.

In Col. 24, line 9 (approx.), Claim 12, please delete "one(5d)," and insert --one (5d),--, therefor.

In Col. 24, line 12 (approx.), Claim 12, please delete "one(5e)," and insert --one (5e),--, therefor.

In Col. 24, line 16 (approx.), Claim 12, please delete "one(5f)," and insert --one (5f),--, therefor.

In Col. 24, line 19 (approx.), Claim 12, please delete "one(5g)," and insert --one (5g),--, therefor.

UNITED STATES PATENT AND TRADEMARK OFFICE
CERTIFICATE OF CORRECTION

PATENT NO.        : 7,312,210 B2
APPLICATION NO.   : 11/367223
DATED             : December 25, 2007
INVENTOR(S)       : Kamal et al.

It is certified that error appears in the above-identified patent and that said Letters Patent is hereby corrected as shown below:

In Col. 24, line 21 (approx.), Claim 12, please delete "oxy }" and insert --oxy--, therefor.

In Col. 24, line 22 (approx.), Claim 12, please delete "one(5h)," and insert --one (5h),--, therefor.

In Col. 24, line 25 (approx.), Claim 12, please delete "one(5i)," and insert --one (5i),--, therefor.

In Col. 24, line 29 (approx.), Claim 12, please delete "benzodiazepine" and insert --benzodiazepin--, therefor.

In Col. 24, line 29 (approx.), Claim 12, please delete "one(5j)," and insert --one (5j),--, therefor.

In Col. 24, line 32 (approx.), Claim 12, please delete "one(5k)," and insert --one (5k),--, therefor.

In Col. 24, line 35 (approx.), Claim 12, please delete "one(5l)," and insert --one (5l),--, therefor.

Signed and Sealed this

Thirtieth Day of December, 2008

JON W. DUDAS
*Director of the United States Patent and Trademark Office*